(12) United States Patent
Nesbitt

(10) Patent No.: US 8,814,862 B2
(45) Date of Patent: *Aug. 26, 2014

(54) ELECTROSURGICAL ELECTRODE AND METHOD OF MANUFACTURING SAME

(75) Inventor: Bruce Nesbitt, Chicago, IL (US)

(73) Assignee: Innovatech, LLC, Chicago, IL (US)

( * ) Notice: Subject to any disclaimer, the term of this patent is extended or adjusted under 35 U.S.C. 154(b) by 1424 days.

This patent is subject to a terminal disclaimer.

(21) Appl. No.: 11/637,445

(22) Filed: Dec. 11, 2006

(65) Prior Publication Data

US 2007/0118113 A1 May 24, 2007

Related U.S. Application Data

(62) Division of application No. 11/127,545, filed on May 12, 2005, now Pat. No. 7,147,634.

(51) Int. Cl.
*A61B 18/14* (2006.01)
*A61B 18/00* (2006.01)

(52) U.S. Cl.
CPC ..... *A61B 18/1402* (2013.01); *A61B 2018/0013* (2013.01)
USPC .......................................................... 606/45

(58) Field of Classification Search
USPC ............................................... 606/41, 45–50
See application file for complete search history.

(56) References Cited

U.S. PATENT DOCUMENTS

| | | |
|---|---|---|
| 3,990,998 A | 11/1976 | DeLuca et al. |
| 4,023,912 A | 5/1977 | Mahler et al. |
| 4,031,286 A | 6/1977 | Seymus |
| 4,038,234 A | 7/1977 | Birchall et al. |
| 4,043,966 A | 8/1977 | Edwards et al. |
| 4,049,863 A | 9/1977 | Vassiliou |
| 4,054,705 A | 10/1977 | Vassiliou |
| 4,056,650 A | 11/1977 | Dates et al. |
| 4,063,068 A | 12/1977 | Johnson et al. |
| 4,066,817 A | 1/1978 | De Rossi |
| 4,070,525 A | 1/1978 | Vassiliou et al. |
| 4,074,718 A | 2/1978 | Morrison, Jr. |
| 4,083,756 A | 4/1978 | Tajkowski |
| 4,087,394 A | 5/1978 | Concannon |

(Continued)

FOREIGN PATENT DOCUMENTS

| | | |
|---|---|---|
| EP | 0003760 | 9/1979 |
| EP | 0010868 | 5/1980 |

(Continued)

OTHER PUBLICATIONS

"Basics of Design Engineering" published by Penton Media, Inc. in 1999.

(Continued)

*Primary Examiner* — Michael Peffley
(74) *Attorney, Agent, or Firm* — Neal, Gerber & Eisenberg LLP

(57) ABSTRACT

An electrosurgical device coated with powder coatings including a silicone resin and siloxane additive without fluoropolymers. In the powder coatings, the silicone resin is methyl phenyl silicone or phenyl silicone or methyl polysiloxane or phenyl alkyl polysiloxane resin and the additive is either methyl alkyl polysiloxane or dimethyl polysiloxane. This coating is applied to the surfaces of an electrosurgical device minimize the build-up of charred tissue on the surfaces of the electrosurgical device.

66 Claims, 6 Drawing Sheets
(2 of 6 Drawing Sheet(s) Filed in Color)

(56) References Cited

U.S. PATENT DOCUMENTS

| | | |
|---|---|---|
| 4,090,993 A | 5/1978 | Attwood et al. |
| 4,098,756 A | 7/1978 | Miller et al. |
| 4,103,076 A | 7/1978 | Ulam |
| 4,105,616 A | 8/1978 | Patton |
| 4,118,537 A | 10/1978 | Vary et al. |
| 4,120,608 A | 10/1978 | Vassiliou |
| 4,121,000 A | 10/1978 | Wald |
| 4,122,226 A | 10/1978 | Vassiliou |
| 4,123,401 A | 10/1978 | Berghmans et al. |
| 4,126,728 A | 11/1978 | Holleran et al. |
| 4,130,675 A | 12/1978 | Vassiliou et al. |
| 4,131,711 A | 12/1978 | Attwood |
| 4,139,576 A | 2/1979 | Yoshimura et al. |
| 4,147,684 A | 4/1979 | Patton |
| 4,147,819 A | 4/1979 | Hukumoto et al. |
| 4,149,455 A | 4/1979 | Ross |
| 4,150,008 A | 4/1979 | Vassiliou et al. |
| 4,155,788 A | 5/1979 | Crandall et al. |
| 4,158,080 A | 6/1979 | Wexell |
| 4,158,081 A | 6/1979 | Wexell |
| 4,167,606 A | 9/1979 | Ulam |
| 4,168,334 A | 9/1979 | Crandall et al. |
| 4,176,222 A | 11/1979 | Cinderey et al. |
| 4,177,320 A | 12/1979 | Yoshimura et al. |
| 4,180,609 A | 12/1979 | Vassiliou |
| 4,181,686 A | 1/1980 | Vassiliou |
| 4,194,042 A | 3/1980 | Dates et al. |
| 4,204,021 A | 5/1980 | Becker |
| 4,223,069 A | 9/1980 | Berghmans |
| 4,226,646 A | 10/1980 | Vassiliou |
| 4,228,219 A | 10/1980 | Hoy et al. |
| 4,230,758 A | 10/1980 | Nagai et al. |
| 4,244,802 A | 1/1981 | Pohto et al. |
| 4,252,702 A | 2/1981 | Wald |
| 4,252,859 A | 2/1981 | Concannon et al. |
| 4,259,375 A | 3/1981 | Vassiliou |
| 4,262,043 A | 4/1981 | Wald |
| 4,264,337 A | 4/1981 | Fenster et al. |
| 4,276,350 A | 6/1981 | Franz |
| 4,277,522 A | 7/1981 | Dorfeld |
| 4,285,728 A | 8/1981 | Babcock et al. |
| 4,287,112 A | 9/1981 | Berghmans |
| 4,296,217 A | 10/1981 | Stuart-Webb |
| 4,301,213 A | 11/1981 | Davies |
| 4,311,634 A | 1/1982 | Vassiliou |
| 4,311,755 A | 1/1982 | Rummel |
| 4,314,559 A * | 2/1982 | Allen ............................... 606/45 |
| 4,316,070 A | 2/1982 | Prosise et al. |
| 4,320,699 A | 3/1982 | Binks |
| 4,321,174 A | 3/1982 | Hoy et al. |
| 4,324,715 A | 4/1982 | Emerick |
| 4,324,836 A | 4/1982 | Patton |
| 4,325,860 A | 4/1982 | Johnson |
| 4,330,453 A | 5/1982 | Patton |
| 4,331,798 A | 5/1982 | Staniland |
| 4,338,360 A | 7/1982 | Cavanagh et al. |
| 4,347,722 A | 9/1982 | Ulam |
| 4,350,259 A | 9/1982 | Cartossi |
| 4,351,882 A | 9/1982 | Concannon |
| 4,352,905 A | 10/1982 | Patton |
| 4,353,950 A | 10/1982 | Vassiliou |
| 4,360,567 A | 11/1982 | Guillevic |
| 4,361,622 A | 11/1982 | Theisen et al. |
| 4,369,346 A | 1/1983 | Hart et al. |
| 4,371,451 A | 2/1983 | Scotti et al. |
| 4,383,067 A | 5/1983 | Patton |
| RE31,448 E | 11/1983 | Attwood et al. |
| 4,413,767 A | 11/1983 | Hellinger |
| 4,425,164 A | 1/1984 | Bliznak et al. |
| 4,425,448 A | 1/1984 | Concannon et al. |
| 4,434,197 A | 2/1984 | Petriello et al. |
| 4,443,574 A | 4/1984 | Coq et al. |
| 4,469,596 A | 9/1984 | Kantor |
| 4,470,688 A | 9/1984 | Inagaki et al. |
| 4,477,517 A | 10/1984 | Rummel |
| 4,478,965 A | 10/1984 | Concannon et al. |
| 4,481,251 A | 11/1984 | Vratny |
| 4,486,508 A | 12/1984 | Coughlin et al. |
| 4,503,168 A | 3/1985 | Hartsing, Jr. |
| 4,507,338 A | 3/1985 | Freundlich |
| 4,512,215 A | 4/1985 | Krauchick |
| 4,514,492 A | 4/1985 | LeStrange et al. |
| 4,515,703 A | 5/1985 | Haq |
| 4,517,975 A | 5/1985 | Garito et al. |
| 4,524,751 A | 6/1985 | Hoglund |
| 4,537,800 A | 8/1985 | Kuziemka |
| 4,541,411 A | 9/1985 | Woolf |
| 4,544,692 A | 10/1985 | Kuziemka |
| 4,547,923 A | 10/1985 | DeVries et al. |
| 4,554,025 A | 11/1985 | Burke et al. |
| 4,575,429 A | 3/1986 | Jacobson |
| 4,576,842 A | 3/1986 | Hartsing et al. |
| 4,585,705 A | 4/1986 | Broderick et al. |
| 4,589,925 A | 5/1986 | Young |
| 4,596,236 A | 6/1986 | Eide |
| 4,598,003 A | 7/1986 | Renholts |
| 4,610,918 A | 9/1986 | Effenberger et al. |
| 4,623,546 A | 11/1986 | Holay et al. |
| 4,623,565 A | 11/1986 | Huybrechts et al. |
| 4,635,538 A | 1/1987 | Polster |
| 4,646,935 A | 3/1987 | Ulam |
| 4,653,468 A | 3/1987 | Lemme et al. |
| 4,664,978 A | 5/1987 | Wu et al. |
| 4,673,468 A | 6/1987 | Myers et al. |
| 4,676,151 A | 6/1987 | Gorsuch et al. |
| 4,677,147 A | 6/1987 | Swihart et al. |
| 4,681,908 A | 7/1987 | Broderick et al. |
| 4,683,168 A | 7/1987 | Hares et al. |
| 4,684,577 A | 8/1987 | Coq |
| 4,701,585 A | 10/1987 | Stewart |
| 4,711,802 A | 12/1987 | Tannenbaum |
| 4,720,941 A | 1/1988 | Belieff et al. |
| 4,737,389 A | 4/1988 | Hartsing, Jr. et al. |
| 4,743,300 A | 5/1988 | Brinduse et al. |
| 4,744,994 A | 5/1988 | Bernacchi et al. |
| 4,747,683 A | 5/1988 | Doane |
| 4,753,742 A | 6/1988 | Wilhelm, Jr. |
| 4,753,848 A | 6/1988 | Sugerman et al. |
| 4,781,970 A | 11/1988 | Barbee et al. |
| 4,785,807 A | 11/1988 | Blanch |
| 4,786,513 A | 11/1988 | Monforton et al. |
| 4,797,521 A | 1/1989 | Liwski |
| 4,830,910 A | 5/1989 | Larson |
| 4,848,337 A | 7/1989 | Shaw et al. |
| 4,851,287 A | 7/1989 | Hartsing, Jr. |
| 4,853,278 A | 8/1989 | Batzar |
| 4,864,089 A | 9/1989 | Tighe et al. |
| 4,873,140 A | 10/1989 | McIntyre |
| 4,876,110 A * | 10/1989 | Blanch ........................ 427/2.28 |
| 4,876,423 A | 10/1989 | Tighe et al. |
| 4,880,951 A | 11/1989 | Levinson |
| 4,895,766 A | 1/1990 | Saad |
| 4,900,594 A | 2/1990 | Quick et al. |
| 4,900,710 A | 2/1990 | Soukiassian et al. |
| 4,910,086 A | 3/1990 | Kawakami et al. |
| 4,923,755 A | 5/1990 | Witucki |
| 4,929,691 A | 5/1990 | Fillmore et al. |
| 4,929,703 A | 5/1990 | Narula et al. |
| 4,940,635 A | 7/1990 | Andrieu et al. |
| 4,943,389 A | 7/1990 | Weete et al. |
| 4,948,603 A | 8/1990 | Bernacchi et al. |
| 4,959,516 A | 9/1990 | Tighe et al. |
| 4,961,996 A | 10/1990 | Carre et al. |
| 4,983,555 A | 1/1991 | Roy et al. |
| 4,987,157 A | 1/1991 | Smart et al. |
| 4,992,212 A | 2/1991 | Corring et al. |
| 5,004,034 A | 4/1991 | Park et al. |
| 5,008,121 A | 4/1991 | Bernacchi et al. |
| 5,016,401 A | 5/1991 | Mangus |
| 5,021,373 A | 6/1991 | Mitchell et al. |
| 5,026,620 A | 6/1991 | Masaki et al. |
| 5,030,218 A | 7/1991 | Alexander |
| 5,037,701 A | 8/1991 | Carre et al. |
| 5,048,688 A | 9/1991 | Hicks, Jr. |

(56) References Cited

U.S. PATENT DOCUMENTS

| | | |
|---|---|---|
| 5,049,437 A | 9/1991 | Tannenbaum |
| 5,066,767 A | 11/1991 | Matzner et al. |
| 5,069,937 A | 12/1991 | Wall |
| 5,071,695 A | 12/1991 | Tannenbaum |
| 5,076,952 A | 12/1991 | Ahmed et al. |
| 5,078,082 A | 1/1992 | Van Dyk Soerewyn |
| 5,078,791 A | 1/1992 | Singh et al. |
| 5,079,073 A | 1/1992 | Tannenbaum |
| 5,079,289 A | 1/1992 | Layton et al. |
| 5,079,397 A | 1/1992 | Keefer |
| 5,089,594 A | 2/1992 | Stern et al. |
| 5,100,402 A | 3/1992 | Fan |
| 5,110,681 A | 5/1992 | Satake et al. |
| 5,122,484 A | 6/1992 | Beall et al. |
| 5,130,510 A | 7/1992 | Zeigler et al. |
| 5,137,956 A | 8/1992 | Trivett |
| 5,141,800 A | 8/1992 | Effenberger et al. |
| 5,143,750 A | 9/1992 | Yamagata et al. |
| 5,145,898 A | 9/1992 | Narula et al. |
| 5,147,967 A | 9/1992 | Stern et al. |
| 5,152,809 A | 10/1992 | Mattesky |
| 5,160,791 A | 11/1992 | Tannenbaum |
| 5,166,000 A | 11/1992 | Singh et al. |
| 5,168,013 A | 12/1992 | Tannenbaum |
| 5,168,107 A | 12/1992 | Tannenbaum |
| 5,169,675 A | 12/1992 | Bartoszek-Loza et al. |
| 5,176,418 A | 1/1993 | Niu |
| 5,177,126 A | 1/1993 | Moore et al. |
| 5,185,184 A | 2/1993 | Koran et al. |
| 5,197,962 A | 3/1993 | Sansom et al. |
| 5,204,126 A | 4/1993 | Singh et al. |
| 5,211,991 A | 5/1993 | Bullock |
| 5,216,092 A | 6/1993 | Huspeni et al. |
| 5,225,274 A | 7/1993 | Ogawa et al. |
| 5,230,961 A | 7/1993 | Tannenbaum |
| 5,232,609 A | 8/1993 | Badinier et al. |
| 5,234,718 A | 8/1993 | Mino et al. |
| 5,238,045 A | 8/1993 | Park et al. |
| 5,238,746 A | 8/1993 | Soga et al. |
| 5,238,985 A | 8/1993 | O'Lenick, Jr. |
| 5,240,774 A | 8/1993 | Ogawa et al. |
| 5,240,775 A | 8/1993 | Tannenbaum |
| 5,246,782 A | 9/1993 | Kennedy et al. |
| 5,246,890 A | 9/1993 | Aitken et al. |
| 5,250,356 A | 10/1993 | Batzar |
| 5,262,241 A | 11/1993 | Huggins |
| 5,270,080 A | 12/1993 | Mino et al. |
| 5,270,269 A | 12/1993 | Hares et al. |
| 5,273,827 A | 12/1993 | Francis |
| 5,312,858 A | 5/1994 | Folsom |
| 5,315,083 A | 5/1994 | Green |
| 5,320,879 A | 6/1994 | Bullock |
| 5,324,566 A | 6/1994 | Ogawa et al. |
| 5,338,579 A | 8/1994 | Ogawa et al. |
| 5,351,608 A | 10/1994 | Muchin et al. |
| 5,380,320 A | 1/1995 | Morris |
| 5,380,557 A | 1/1995 | Spiro |
| 5,382,247 A | 1/1995 | Cimino et al. |
| 5,385,785 A | 1/1995 | Lovell |
| 5,388,732 A | 2/1995 | Greger |
| 5,389,767 A | 2/1995 | Dobry |
| 5,391,594 A | 2/1995 | Romenesko et al. |
| 5,393,568 A | 2/1995 | Valente et al. |
| 5,396,052 A | 3/1995 | Petcavich et al. |
| 5,407,598 A | 4/1995 | Olson et al. |
| 5,411,014 A | 5/1995 | Paul |
| 5,411,771 A | 5/1995 | Tsai |
| 5,415,626 A | 5/1995 | Goodman et al. |
| 5,423,247 A | 6/1995 | Rodrigues-Ely |
| 5,435,839 A | 7/1995 | Ogawa |
| 5,440,973 A | 8/1995 | Welhouse |
| 5,441,169 A | 8/1995 | Petty |
| 5,460,661 A | 10/1995 | Maynard, Jr. |
| 5,462,769 A | 10/1995 | Tsai |
| 5,466,486 A | 11/1995 | Ogawa et al. |
| 5,468,798 A | 11/1995 | Leech |
| 5,471,731 A | 12/1995 | Welhouse |
| 5,473,018 A | 12/1995 | Namura et al. |
| 5,476,552 A | 12/1995 | Tucker et al. |
| 5,478,651 A | 12/1995 | Tannenbaum |
| 5,480,930 A | 1/1996 | Gentle et al. |
| 5,484,467 A | 1/1996 | Nass et al. |
| 5,486,683 A | 1/1996 | Shimizu et al. |
| 5,491,116 A | 2/1996 | Beall et al. |
| 5,492,729 A | 2/1996 | Tufty-Wisniewski et al. |
| 5,492,769 A | 2/1996 | Pryor et al. |
| 5,496,270 A | 3/1996 | Nettekoven |
| 5,496,315 A | 3/1996 | Weaver et al. |
| 5,499,597 A | 3/1996 | Kronberg |
| 5,518,543 A | 5/1996 | Pietrowski et al. |
| 5,519,196 A | 5/1996 | Xu |
| 5,531,743 A | 7/1996 | Nettekoven et al. |
| 5,532,460 A | 7/1996 | Okato et al. |
| 5,535,904 A | 7/1996 | Tucker |
| 5,544,568 A | 8/1996 | Potgieter |
| 5,545,255 A | 8/1996 | Ogawa |
| 5,545,439 A | 8/1996 | Deng et al. |
| 5,552,112 A | 9/1996 | Schiffmann et al. |
| 5,554,415 A | 9/1996 | Turchan et al. |
| 5,554,681 A | 9/1996 | Patel |
| 5,557,927 A | 9/1996 | Chiang et al. |
| 5,560,978 A | 10/1996 | Leech |
| 5,562,659 A * | 10/1996 | Morris ............................ 606/41 |
| 5,562,991 A | 10/1996 | Tannenbaum |
| 5,572,846 A | 11/1996 | Sosa |
| 5,575,012 A | 11/1996 | Fox et al. |
| 5,578,136 A | 11/1996 | Taylor et al. |
| 5,579,725 A | 12/1996 | Boshears |
| 5,588,634 A | 12/1996 | Nettekoven |
| D377,524 S | 1/1997 | Lipp |
| 5,591,141 A | 1/1997 | Nettekoven |
| 5,605,660 A | 2/1997 | Buongiorno et al. |
| 5,609,431 A | 3/1997 | Carroll |
| 5,620,754 A | 4/1997 | Turchan et al. |
| 5,626,907 A | 5/1997 | Hagiwara et al. |
| 5,628,426 A | 5/1997 | Doyle et al. |
| 5,632,924 A | 5/1997 | Gics et al. |
| 5,633,090 A | 5/1997 | Rodek et al. |
| 5,637,641 A | 6/1997 | Becker et al. |
| 5,643,256 A | 7/1997 | Urueta |
| 5,643,485 A | 7/1997 | Potter et al. |
| 5,645,748 A | 7/1997 | Schiffmann et al. |
| 5,662,026 A | 9/1997 | Prakasa |
| 5,667,846 A | 9/1997 | Thomas |
| 5,667,891 A | 9/1997 | Batzar et al. |
| 5,670,010 A | 9/1997 | Hagiwara et al. |
| 5,679,273 A | 10/1997 | Petetin |
| 5,686,160 A | 11/1997 | Yamada et al. |
| 5,691,067 A * | 11/1997 | Patel ............................ 428/447 |
| 5,691,756 A | 11/1997 | Rise et al. |
| 5,693,050 A | 12/1997 | Speiser |
| 5,693,052 A | 12/1997 | Weaver |
| 5,697,926 A | 12/1997 | Weaver |
| 5,702,387 A * | 12/1997 | Arts et al. ...................... 606/45 |
| 5,703,030 A | 12/1997 | Perkins et al. |
| 5,703,034 A | 12/1997 | Offshack et al. |
| 5,705,464 A | 1/1998 | Scheper et al. |
| 5,707,688 A | 1/1998 | Batzar et al. |
| 5,711,995 A | 1/1998 | Batzar |
| 5,713,895 A | 2/1998 | Lontine et al. |
| 5,718,963 A | 2/1998 | Batzar |
| 5,721,053 A | 2/1998 | Thomas |
| 5,723,945 A | 3/1998 | Schermerhorn |
| 5,726,247 A | 3/1998 | Michalczyk et al. |
| 5,728,455 A | 3/1998 | Batzar |
| 5,730,922 A | 3/1998 | Babb et al. |
| 5,731,046 A | 3/1998 | Mistry et al. |
| 5,752,951 A | 5/1998 | Yanik |
| 5,753,313 A | 5/1998 | Tsai |
| 5,766,698 A | 6/1998 | Singh et al. |
| 5,770,640 A | 6/1998 | Ogawa |
| 5,789,083 A | 8/1998 | Thomas |
| 5,792,109 A | 8/1998 | Ladd |
| 5,792,544 A | 8/1998 | Klein |

(56) References Cited

U.S. PATENT DOCUMENTS

| | | | |
|---|---|---|---|
| 5,792,570 A | 8/1998 | Ishikawa et al. |
| 5,798,326 A | 8/1998 | Goldstein et al. |
| 5,804,542 A | 9/1998 | Scheper et al. |
| 5,814,392 A | 9/1998 | You et al. |
| D399,561 S | 10/1998 | Ellingson |
| 5,817,419 A | 10/1998 | Fryd et al. |
| 5,823,204 A | 10/1998 | Todd |
| 5,827,573 A | 10/1998 | Tsai |
| 5,830,529 A | 11/1998 | Ross |
| 5,832,636 A | 11/1998 | Lyden et al. |
| D402,030 S | 12/1998 | Roberts et al. |
| D402,031 S | 12/1998 | Roberts et al. |
| 5,843,080 A | 12/1998 | Fleenor et al. |
| 5,846,237 A | 12/1998 | Nettekoven |
| 5,849,369 A | 12/1998 | Ogawa |
| 5,849,829 A | 12/1998 | Buegman |
| 5,858,941 A | 1/1999 | Oakes et al. |
| 5,863,608 A | 1/1999 | Swisher et al. |
| 5,872,168 A | 2/1999 | Katoot |
| 5,880,205 A | 3/1999 | Tannenbaum |
| 5,885,280 A | 3/1999 | Nettekoven et al. |
| 5,885,281 A | 3/1999 | Urueta |
| 5,893,849 A | 4/1999 | Weaver |
| 5,900,459 A | 5/1999 | Selley et al. |
| 5,902,301 A | 5/1999 | Olig |
| 5,902,781 A | 5/1999 | Painter |
| 5,906,871 A | 5/1999 | Takebe et al. |
| 5,910,459 A | 6/1999 | Beall et al. |
| 5,913,315 A | 6/1999 | Todd |
| 5,916,952 A | 6/1999 | Romenesko et al. |
| 5,921,173 A | 7/1999 | Grycan et al. |
| 5,922,271 A | 7/1999 | Semar et al. |
| 5,922,468 A | 7/1999 | Huesmann et al. |
| 5,924,592 A | 7/1999 | Hieronymus |
| 5,925,039 A | 7/1999 | Landingham |
| 5,925,043 A | 7/1999 | Kumar et al. |
| 5,947,808 A | 9/1999 | Adams |
| 5,951,494 A | 9/1999 | Wang et al. |
| 5,955,149 A | 9/1999 | Kuziemka |
| 5,968,881 A | 10/1999 | Haeggberg et al. |
| 5,972,494 A | 10/1999 | Janssens |
| 5,988,385 A | 11/1999 | Stephens |
| 5,997,517 A | 12/1999 | Whitbourne |
| 6,001,205 A | 12/1999 | Mauro |
| 6,004,317 A | 12/1999 | Speiser |
| 6,004,318 A | 12/1999 | Garito et al. |
| 6,007,735 A | 12/1999 | Creed |
| 6,013,331 A | 1/2000 | Ogawa |
| 6,020,294 A | 2/2000 | Getty et al. |
| 6,030,381 A * | 2/2000 | Jones et al. ............... 606/41 |
| 6,039,735 A | 3/2000 | Greep |
| 6,045,592 A | 4/2000 | Paquin |
| 6,053,178 A | 4/2000 | Todd |
| 6,053,910 A | 4/2000 | Fleenor |
| 6,060,167 A | 5/2000 | Morgan et al. |
| 6,063,207 A | 5/2000 | Yu et al. |
| 6,066,137 A | 5/2000 | Greep |
| 6,070,444 A | 6/2000 | Lontine et al. |
| 6,071,283 A | 6/2000 | Nardella et al. |
| 6,073,635 A | 6/2000 | Todd |
| 6,080,496 A | 6/2000 | Hupf et al. |
| 6,083,221 A | 7/2000 | Fleenor et al. |
| 6,090,107 A | 7/2000 | Borgmeier et al. |
| 6,092,459 A | 7/2000 | Zhang |
| 6,103,361 A | 8/2000 | Batzar et al. |
| 6,110,532 A | 8/2000 | Causton et al. |
| 6,114,028 A | 9/2000 | Muchin et al. |
| 6,115,539 A | 9/2000 | Cohn |
| 6,123,999 A | 9/2000 | Felix et al. |
| 6,124,223 A | 9/2000 | Beall et al. |
| 6,124,575 A | 9/2000 | Black |
| 6,132,427 A | 10/2000 | Jones et al. |
| 6,133,359 A | 10/2000 | Bate et al. |
| 6,143,707 A | 11/2000 | Trinh et al. |
| 6,146,556 A | 11/2000 | Katoot |
| 6,159,412 A | 12/2000 | Fletcher et al. |
| 6,171,652 B1 | 1/2001 | Singh et al. |
| 6,173,839 B1 | 1/2001 | Dieter et al. |
| 6,174,309 B1 | 1/2001 | Wrublewski et al. |
| 6,177,655 B1 | 1/2001 | Toman |
| 6,189,722 B1 | 2/2001 | Ason |
| 6,197,438 B1 | 3/2001 | Faulkner |
| 6,207,631 B1 | 3/2001 | Kasturi et al. |
| 6,214,000 B1 | 4/2001 | Fleenor et al. |
| 6,217,656 B1 | 4/2001 | Spiering et al. |
| 6,220,617 B1 | 4/2001 | Hunger |
| 6,221,739 B1 | 4/2001 | Gorelik |
| 6,227,955 B1 | 5/2001 | Custer et al. |
| 6,228,753 B1 | 5/2001 | Lo et al. |
| 6,232,372 B1 | 5/2001 | Brothers et al. |
| 6,238,798 B1 | 5/2001 | Kang et al. |
| 6,244,483 B1 | 6/2001 | McLemore et al. |
| 6,245,431 B1 | 6/2001 | Griswold et al. |
| 6,245,833 B1 | 6/2001 | Kang et al. |
| 6,248,435 B1 | 6/2001 | Leck |
| 6,254,699 B1 | 7/2001 | Hermanek |
| 6,257,752 B1 | 7/2001 | Browne |
| 6,258,201 B1 | 7/2001 | Krech |
| 6,258,418 B1 | 7/2001 | Rudder et al. |
| 6,258,758 B1 | 7/2001 | Greer |
| 6,261,985 B1 | 7/2001 | Hsu |
| 6,267,047 B1 | 7/2001 | Mosher, II et al. |
| 6,270,831 B2 | 8/2001 | Kumar et al. |
| 6,270,836 B1 | 8/2001 | Holman |
| 6,270,903 B1 | 8/2001 | Feng et al. |
| 6,277,811 B1 | 8/2001 | Kasturi et al. |
| 6,287,632 B1 | 9/2001 | Nishio et al. |
| 6,291,054 B1 | 9/2001 | Thomas et al. |
| 6,291,084 B1 | 9/2001 | Darolia et al. |
| 6,297,564 B1 | 10/2001 | Chung |
| 6,306,176 B1 | 10/2001 | Whitbourne |
| 6,309,583 B1 | 10/2001 | Feldstein |
| 6,312,814 B1 | 11/2001 | Kolouch |
| 6,320,169 B1 | 11/2001 | Clothier |
| 6,331,328 B1 | 12/2001 | Cheng |
| 6,332,490 B1 | 12/2001 | Griggs |
| 6,349,632 B1 | 2/2002 | Beck, Jr. |
| 6,360,423 B1 | 3/2002 | Groll |
| 6,360,654 B1 | 3/2002 | Cornfield |
| 6,364,130 B2 | 4/2002 | Wright |
| 6,371,012 B2 | 4/2002 | Sawyer |
| 6,372,708 B1 | 4/2002 | Kasturi et al. |
| 6,376,450 B1 | 4/2002 | Ghosh et al. |
| 6,382,454 B1 | 5/2002 | Buffard et al. |
| 6,398,060 B1 | 6/2002 | Apostolides |
| 6,399,924 B1 | 6/2002 | Cai |
| 6,402,636 B1 | 6/2002 | Chang |
| 6,403,164 B1 | 6/2002 | Jonschker et al. |
| 6,403,213 B1 | 6/2002 | Huesmann |
| 6,409,725 B1 * | 6/2002 | Khandkar et al. ............... 606/45 |
| 6,427,904 B1 | 8/2002 | Groll |
| 6,429,161 B1 | 8/2002 | Souchard et al. |
| 6,444,257 B1 | 9/2002 | Kutt et al. |
| 6,446,814 B1 | 9/2002 | King |
| 6,454,456 B2 | 9/2002 | Browne |
| 6,454,764 B1 | 9/2002 | Fleenor et al. |
| 6,468,642 B1 | 10/2002 | Bray et al. |
| 6,475,253 B2 | 11/2002 | Culler et al. |
| 6,475,939 B1 | 11/2002 | Souchard et al. |
| 6,479,581 B1 | 11/2002 | Ireland et al. |
| 6,488,971 B1 | 12/2002 | Miller et al. |
| 6,491,195 B1 | 12/2002 | McLemore et al. |
| 6,491,762 B1 | 12/2002 | Bundy et al. |
| 6,511,479 B2 | 1/2003 | Gentelia et al. |
| 6,511,931 B1 | 1/2003 | Baldwin |
| 6,515,263 B2 | 2/2003 | Mitra et al. |
| 6,518,337 B1 | 2/2003 | Baker et al. |
| 6,518,349 B1 | 2/2003 | Felix et al. |
| 6,526,876 B2 | 3/2003 | Kahler et al. |
| 6,528,476 B1 | 3/2003 | Bodet et al. |
| 6,528,768 B1 | 3/2003 | Simic-Glavaski et al. |
| 6,531,557 B1 | 3/2003 | Hosokawa et al. |
| 6,536,109 B2 | 3/2003 | Berthelet et al. |
| 6,544,258 B2 | 4/2003 | Fleenor et al. |

(56) References Cited

U.S. PATENT DOCUMENTS

| | | |
|---|---|---|
| 6,544,669 B2 | 4/2003 | Groll |
| 6,557,732 B2 | 5/2003 | Van Rompuy et al. |
| 6,566,289 B2 | 5/2003 | Aronica et al. |
| 6,573,234 B1 | 6/2003 | Sivik et al. |
| 6,576,038 B1 | 6/2003 | Rao |
| 6,582,424 B2 | 6/2003 | Fleenor et al. |
| 6,596,380 B1 | 7/2003 | Buffard et al. |
| 6,606,988 B2 | 8/2003 | Clark |
| 6,607,528 B1 | 8/2003 | Quick et al. |
| 6,607,614 B1 | 8/2003 | Richardson et al. |
| 6,610,386 B2 | 8/2003 | Williams et al. |
| 6,613,860 B1 | 9/2003 | Dams et al. |
| 6,620,463 B2 | 9/2003 | Stay |
| 6,626,901 B1 | 9/2003 | Treat et al. |
| 6,630,650 B2 | 10/2003 | Bassill et al. |
| 6,638,600 B2 | 10/2003 | Gazo et al. |
| 6,648,983 B1 | 11/2003 | Cardola et al. |
| 6,649,891 B1 | 11/2003 | Kitko et al. |
| 6,656,258 B2 | 12/2003 | Elsbernd et al. |
| 6,656,897 B1 | 12/2003 | Cardola et al. |
| 6,670,314 B2 | 12/2003 | Smith et al. |
| 6,677,563 B2 | 1/2004 | Lai |
| 6,683,036 B2 | 1/2004 | Foley et al. |
| 6,685,704 B2 | 2/2004 | Greep |
| 6,693,071 B2 | 2/2004 | Ghosh et al. |
| 6,712,497 B2 | 3/2004 | Jersey et al. |
| 6,715,631 B2 | 4/2004 | Kim |
| 6,723,692 B2 | 4/2004 | Foley et al. |
| 6,725,505 B2 | 4/2004 | Willat |
| 6,729,479 B2 | 5/2004 | Morgan |
| 6,733,697 B2 | 5/2004 | Rhodes et al. |
| 6,737,164 B2 | 5/2004 | Araki et al. |
| 6,737,489 B2 | 5/2004 | Linert et al. |
| 6,740,628 B2 | 5/2004 | Bennie et al. |
| 6,749,081 B2 | 6/2004 | Cheng |
| 6,750,187 B2 | 6/2004 | Alam et al. |
| 6,752,303 B2 | 6/2004 | McLemore et al. |
| 6,758,914 B2 | 7/2004 | Kool et al. |
| 6,761,645 B1 | 7/2004 | Weber |
| 6,761,964 B2 | 7/2004 | Tannenbaum |
| 6,770,287 B1 | 8/2004 | Sun et al. |
| 6,780,227 B2 | 8/2004 | DuBose et al. |
| 6,783,525 B2 | 8/2004 | Greep et al. |
| 6,787,515 B2 | 9/2004 | Foley et al. |
| 6,793,093 B2 | 9/2004 | Tsai |
| 6,794,550 B2 | 9/2004 | Hintzer et al. |
| 6,797,223 B2 | 9/2004 | Beale et al. |
| 6,808,806 B2 | 10/2004 | Phillips et al. |
| 6,818,299 B2 | 11/2004 | Phillips et al. |
| 6,820,541 B2 | 11/2004 | Siegel et al. |
| 6,821,940 B2 | 11/2004 | Bullock et al. |
| 6,822,059 B2 | 11/2004 | Buckanin et al. |
| 6,828,527 B2 | 12/2004 | Simic-Glavaski et al. |
| 6,830,221 B1 | 12/2004 | Janson et al. |
| 6,831,027 B2 | 12/2004 | Gazo |
| 6,831,053 B1 | 12/2004 | Ghosh et al. |
| 6,833,328 B1 | 12/2004 | Kool et al. |
| 6,833,418 B2 | 12/2004 | Tan et al. |
| 6,838,166 B2 | 1/2005 | Phillips et al. |
| 6,841,594 B2 | 1/2005 | Jones et al. |
| 6,846,570 B2 | 1/2005 | Leech et al. |
| 6,846,760 B2 | 1/2005 | Siebers et al. |
| 6,863,738 B2 | 3/2005 | Kool et al. |
| 6,863,974 B2 | 3/2005 | Shah et al. |
| 6,864,314 B1 | 3/2005 | Yeung et al. |
| 6,884,459 B2 | 4/2005 | Caballero et al. |
| 6,885,306 B2 | 4/2005 | Holzman et al. |
| 6,887,578 B2 | 5/2005 | Gleason et al. |
| 6,893,724 B2 | 5/2005 | Lin et al. |
| 6,896,934 B2 | 5/2005 | Aronica et al. |
| 6,899,923 B2 | 5/2005 | Kimbrell, Jr. et al. |
| 6,901,687 B2 | 6/2005 | Krings et al. |
| 6,905,722 B2 | 6/2005 | Liu |
| 6,906,295 B2 | 6/2005 | Ge |
| 6,911,512 B2 | 6/2005 | Jing et al. |
| 6,913,255 B2 | 7/2005 | Porchia et al. |
| 6,914,223 B2 | 7/2005 | Krause et al. |
| 6,919,012 B1 | 7/2005 | Bucar |
| 6,919,422 B2 | 7/2005 | Gallucci et al. |
| 6,920,820 B2 | 7/2005 | Meggison et al. |
| 6,921,546 B2 | 7/2005 | Albach |
| 6,921,787 B2 | 7/2005 | Bate |
| 6,933,053 B2 | 8/2005 | Alger |
| 6,942,935 B2 | 9/2005 | Ge |
| 6,949,178 B2 | 9/2005 | Tennakoon et al. |
| 6,949,721 B2 | 9/2005 | Simic-Glavaski et al. |
| 6,951,559 B1 | 10/2005 | Greep |
| 6,952,530 B2 | 10/2005 | Helvajian et al. |
| 6,956,016 B2 | 10/2005 | Speed et al. |
| 6,956,078 B2 | 10/2005 | Cavanaugh et al. |
| 6,979,667 B1 | 12/2005 | Kaiser et al. |
| 6,998,375 B2 | 2/2006 | Kapur et al. |
| 7,005,396 B2 | 2/2006 | Espargilliere et al. |
| 7,007,808 B2 | 3/2006 | Morgan |
| 7,008,553 B2 | 3/2006 | Wustman et al. |
| 7,018,727 B2 | 3/2006 | Dzick |
| 7,024,147 B2 | 4/2006 | Sugawara et al. |
| 7,026,036 B2 | 4/2006 | Leech et al. |
| 7,037,550 B2 | 5/2006 | Liu et al. |
| 7,041,728 B2 | 5/2006 | Zipplies et al. |
| 7,041,773 B2 | 5/2006 | Gallucci et al. |
| 7,045,571 B2 | 5/2006 | Tan et al. |
| 7,083,613 B2 | 8/2006 | Treat |
| 7,083,856 B2 | 8/2006 | Rajagopalan et al. |
| 7,093,340 B2 | 8/2006 | Groll |
| 7,104,409 B2 | 9/2006 | Morgan |
| 7,112,764 B2 | 9/2006 | Garcia |
| 7,119,155 B2 | 10/2006 | Chow et al. |
| 7,121,413 B2 | 10/2006 | Morgan |
| 7,125,828 B2 | 10/2006 | Catlin et al. |
| 7,126,755 B2 | 10/2006 | Moon et al. |
| 7,129,310 B2 | 10/2006 | Greene et al. |
| 7,132,377 B2 | 11/2006 | Borgonjon et al. |
| 7,135,122 B2 | 11/2006 | Park |
| 7,147,634 B2 | 12/2006 | Nesbitt |
| 7,160,297 B2 | 1/2007 | Nesbitt |
| 7,168,148 B2 | 1/2007 | Groll |
| 7,169,472 B2 | 1/2007 | Raksha et al. |
| 7,176,158 B2 | 2/2007 | Chow et al. |
| 7,217,907 B2 | 5/2007 | El-Raghy et al. |
| 7,229,600 B2 | 6/2007 | Yadav |
| 7,246,406 B2 | 7/2007 | Yarbrough et al. |
| 7,250,009 B2 | 7/2007 | Weber |
| 7,251,944 B2 | 8/2007 | Holtzapple et al. |
| 7,258,747 B2 | 8/2007 | Vago et al. |
| 7,271,209 B2 | 9/2007 | Li et al. |
| 7,288,091 B2 | 10/2007 | Nesbitt |
| 7,309,412 B2 | 12/2007 | Minevski et al. |
| 7,312,300 B2 | 12/2007 | Mitchell |
| 7,319,083 B2 | 1/2008 | Jin et al. |
| 7,337,518 B2 | 3/2008 | Cheng |
| 7,342,066 B2 | 3/2008 | Dadalas et al. |
| 7,342,081 B2 | 3/2008 | Chandler et al. |
| 7,354,979 B2 | 4/2008 | Brant et al. |
| 7,365,860 B2 | 4/2008 | Price |
| 7,380,288 B1 | 6/2008 | Duncan |
| 7,390,326 B2 | 6/2008 | Nesbitt |
| 7,393,924 B2 | 7/2008 | Vitaliano et al. |
| 7,412,922 B2 | 8/2008 | McLemore |
| 7,413,684 B2 | 8/2008 | Fishburn et al. |
| 7,416,619 B2 | 8/2008 | Lei |
| 7,435,774 B2 | 10/2008 | Williams et al. |
| 7,449,507 B2 | 11/2008 | Fishburn |
| 7,468,333 B2 | 12/2008 | Kimbrell, Jr. et al. |
| 7,469,703 B2 | 12/2008 | France et al. |
| 7,479,327 B2 | 1/2009 | Domine |
| 7,488,511 B2 | 2/2009 | Caballero et al. |
| 7,488,515 B2 | 2/2009 | Groll |
| 7,531,594 B2 | 5/2009 | Lin et al. |
| 7,541,102 B2 | 6/2009 | Klippe et al. |
| 7,544,420 B2 | 6/2009 | Domine et al. |
| 7,563,517 B2 | 7/2009 | Raffy et al. |
| 7,569,132 B2 | 8/2009 | Dolan |
| 7,578,921 B2 | 8/2009 | Dolan |

(56) References Cited

U.S. PATENT DOCUMENTS

| | | |
|---|---|---|
| 7,578,950 B2 | 8/2009 | Kirchner et al. |
| 7,594,594 B2 | 9/2009 | Troost et al. |
| 7,622,523 B2 | 11/2009 | Li et al. |
| 7,629,400 B2 | 12/2009 | Hyman |
| 7,629,416 B2 | 12/2009 | Li et al. |
| 7,635,522 B2 | 12/2009 | Cnossen et al. |
| 7,652,115 B2 | 1/2010 | Dams et al. |
| 7,661,387 B2 | 2/2010 | Poullos |
| 7,678,465 B2 | 3/2010 | Sambasivan et al. |
| 7,718,212 B2 | 5/2010 | Nesbitt |
| 7,733,008 B2 | 6/2010 | Ke et al. |
| 7,737,200 B2 | 6/2010 | Jabar, Jr. et al. |
| 7,765,919 B2 | 8/2010 | Siegel et al. |
| 7,784,638 B2 | 8/2010 | Kishbaugh et al. |
| 2001/0021848 A1 | 9/2001 | Fleenor et al. |
| 2001/0031964 A1 | 10/2001 | Gentelia et al. |
| 2001/0033083 A1 | 10/2001 | Kaposi |
| 2001/0041665 A1 | 11/2001 | Severns et al. |
| 2001/0044019 A1 | 11/2001 | Huesmann |
| 2001/0047968 A1 | 12/2001 | Wright |
| 2002/0003749 A1 | 1/2002 | Browne |
| 2002/0009541 A1 | 1/2002 | Clayton |
| 2002/0037817 A1 | 3/2002 | Foley et al. |
| 2002/0037822 A1 | 3/2002 | Foley et al. |
| 2002/0068014 A1 | 6/2002 | Haught et al. |
| 2002/0093210 A1 | 7/2002 | Sassone et al. |
| 2002/0100493 A1 | 8/2002 | Kool et al. |
| 2002/0111622 A1 | 8/2002 | Khandkar et al. |
| 2002/0113066 A1 | 8/2002 | Stark et al. |
| 2002/0137648 A1 | 9/2002 | Sharma et al. |
| 2002/0142931 A1 | 10/2002 | DeNome et al. |
| 2002/0151398 A1 | 10/2002 | Campbell |
| 2002/0160194 A1 | 10/2002 | Phillips et al. |
| 2002/0160930 A1 | 10/2002 | Emmerson et al. |
| 2002/0163285 A1 | 11/2002 | Vanlandingham |
| 2002/0169090 A1 | 11/2002 | Foley et al. |
| 2002/0182449 A1 | 12/2002 | Neal et al. |
| 2003/0008944 A1 | 1/2003 | Jones et al. |
| 2003/0045437 A1 | 3/2003 | Ward |
| 2003/0049485 A1 | 3/2003 | Brupbacher et al. |
| 2003/0064874 A1 | 4/2003 | Eckmann et al. |
| 2003/0096457 A1 | 5/2003 | Gottschalk et al. |
| 2003/0109864 A1 | 6/2003 | Greep et al. |
| 2003/0109865 A1* | 6/2003 | Greep et al. .............. 606/41 |
| 2003/0119689 A1 | 6/2003 | Hutton et al. |
| 2003/0121421 A1 | 7/2003 | Wey |
| 2003/0121921 A1 | 7/2003 | Burton et al. |
| 2003/0125421 A1 | 7/2003 | Bladel et al. |
| 2003/0126996 A1 | 7/2003 | Cheng |
| 2003/0138661 A1 | 7/2003 | Souchard et al. |
| 2003/0163125 A1 | 8/2003 | Greep |
| 2003/0168416 A1 | 9/2003 | Morgan |
| 2003/0169801 A1 | 9/2003 | Chilton |
| 2003/0184101 A1 | 10/2003 | Nelson |
| 2003/0211618 A1 | 11/2003 | Patel |
| 2003/0226882 A1 | 12/2003 | Porchia et al. |
| 2004/0011245 A1 | 1/2004 | Sambasivan et al. |
| 2004/0011350 A1 | 1/2004 | Dowst et al. |
| 2004/0011795 A1 | 1/2004 | Porchia et al. |
| 2004/0018932 A1 | 1/2004 | Yuriditsky et al. |
| 2004/0036061 A1 | 2/2004 | Rhodes et al. |
| 2004/0040160 A1 | 3/2004 | Cohen et al. |
| 2004/0051208 A1 | 3/2004 | Creekmore |
| 2004/0063601 A1 | 4/2004 | Denome et al. |
| 2004/0067861 A1 | 4/2004 | Denome et al. |
| 2004/0071987 A1 | 4/2004 | Bate |
| 2004/0076846 A1 | 4/2004 | Domine et al. |
| 2004/0079755 A1 | 4/2004 | Graus |
| 2004/0110443 A1 | 6/2004 | Pelham, Sr. |
| 2004/0115477 A1 | 6/2004 | Nesbitt |
| 2004/0116792 A1 | 6/2004 | Nesbitt |
| 2004/0118837 A1 | 6/2004 | Samuels et al. |
| 2004/0137818 A1 | 7/2004 | Kimbrell, Jr. et al. |
| 2004/0138083 A1 | 7/2004 | Kimbrell, Jr. et al. |
| 2004/0143052 A1 | 7/2004 | Epsch et al. |
| 2004/0144065 A1 | 7/2004 | Smith et al. |
| 2004/0147425 A1 | 7/2004 | Castro et al. |
| 2004/0149142 A1 | 8/2004 | Groll |
| 2004/0149311 A1 | 8/2004 | Foley et al. |
| 2004/0152591 A1 | 8/2004 | Jin et al. |
| 2004/0161623 A1 | 8/2004 | Domine et al. |
| 2004/0169013 A1 | 9/2004 | Kool et al. |
| 2004/0226850 A1 | 11/2004 | Behnke et al. |
| 2004/0229079 A1 | 11/2004 | Groll |
| 2004/0253387 A1 | 12/2004 | Cavero |
| 2004/0255792 A1 | 12/2004 | Parker |
| 2004/0259749 A1 | 12/2004 | Braeckman et al. |
| 2005/0025900 A1 | 2/2005 | Cavero |
| 2005/0035086 A1 | 2/2005 | Chen et al. |
| 2005/0065294 A1 | 3/2005 | Cramer |
| 2005/0066996 A1 | 3/2005 | France et al. |
| 2005/0070659 A1 | 3/2005 | Shiow-Ling et al. |
| 2005/0076795 A1 | 4/2005 | Riddle |
| 2005/0107282 A1 | 5/2005 | Ford et al. |
| 2005/0133522 A1 | 6/2005 | Son |
| 2005/0160543 A1 | 7/2005 | Catalfamo et al. |
| 2005/0167435 A1 | 8/2005 | Whitmer |
| 2005/0175786 A1 | 8/2005 | Singh et al. |
| 2005/0181195 A1 | 8/2005 | Dubrow |
| 2005/0191432 A1 | 9/2005 | Hofmans |
| 2005/0192397 A1 | 9/2005 | Dadalas et al. |
| 2005/0193901 A1 | 9/2005 | Buehler |
| 2005/0199133 A1 | 9/2005 | Narula et al. |
| 2005/0211105 A1 | 9/2005 | Hanson |
| 2005/0217496 A1 | 10/2005 | Dodgen |
| 2005/0218004 A1 | 10/2005 | Charles |
| 2005/0228491 A1 | 10/2005 | Snyder et al. |
| 2005/0241089 A1 | 11/2005 | Brunner et al. |
| 2005/0242090 A1 | 11/2005 | Cantu |
| 2005/0249886 A1 | 11/2005 | Ge |
| 2006/0008643 A1 | 1/2006 | Lin et al. |
| 2006/0014876 A1 | 1/2006 | Bushelman et al. |
| 2006/0081235 A1 | 4/2006 | Lundh et al. |
| 2006/0081236 A1 | 4/2006 | Johnston et al. |
| 2006/0081639 A1 | 4/2006 | Lazaroff et al. |
| 2006/0127699 A1 | 6/2006 | Moelle et al. |
| 2006/0135341 A1 | 6/2006 | Ellison et al. |
| 2006/0179594 A1 | 8/2006 | Yeung |
| 2006/0201497 A1 | 9/2006 | Leel |
| 2006/0207289 A1 | 9/2006 | Hale |
| 2006/0216395 A1 | 9/2006 | Franklin |
| 2006/0225725 A1 | 10/2006 | Rinaldo |
| 2006/0246149 A1 | 11/2006 | Buchholz et al. |
| 2006/0281653 A1 | 12/2006 | Hutton et al. |
| 2007/0003712 A1 | 1/2007 | Domine |
| 2007/0054139 A1 | 3/2007 | Domine |
| 2007/0093811 A1 | 4/2007 | Nesbitt |
| 2007/0107821 A1 | 5/2007 | Ness |
| 2007/0219333 A1 | 9/2007 | Shimono et al. |
| 2007/0267958 A1 | 11/2007 | Kitazawa et al. |
| 2007/0292477 A1 | 12/2007 | Kumar |
| 2007/0292706 A1 | 12/2007 | Spring et al. |
| 2008/0237241 A1 | 10/2008 | Buffard et al. |
| 2010/0215834 A1 | 8/2010 | Nesbitt |

FOREIGN PATENT DOCUMENTS

| | | |
|---|---|---|
| EP | 0015720 | 9/1980 |
| EP | 0022256 | 1/1981 |
| EP | 0064348 | 11/1982 |
| EP | 0064374 | 11/1982 |
| EP | 0068695 | 1/1983 |
| EP | 0084771 | 8/1983 |
| EP | 0132078 | 1/1985 |
| EP | 0166243 | 1/1986 |
| EP | 0188065 | 7/1986 |
| EP | 0190926 | 8/1986 |
| EP | 0195229 | 9/1986 |
| EP | 0201268 | 11/1986 |
| EP | 0232441 | 8/1987 |
| EP | 0236517 | 9/1987 |
| EP | 0318204 | 5/1989 |
| EP | 0325779 | 8/1989 |
| EP | 0386379 | 9/1990 |

(56) References Cited

FOREIGN PATENT DOCUMENTS

| | | |
|---|---|---|
| EP | 0386380 | 9/1990 |
| EP | 0390994 | 10/1990 |
| EP | 0395186 | 10/1990 |
| EP | 0424072 | 4/1991 |
| EP | 0429222 | 5/1991 |
| EP | 0444821 | 9/1991 |
| EP | 0 479 482 | 4/1992 |
| EP | 0484001 | 5/1992 |
| EP | 0484746 | 5/1992 |
| EP | 0500361 | 8/1992 |
| EP | 0565743 | 10/1993 |
| EP | 0577951 | 1/1994 |
| EP | 0594374 | 4/1994 |
| EP | 0607934 | 7/1994 |
| EP | 0629673 | 12/1994 |
| EP | 0659853 | 6/1995 |
| EP | 0681013 | 11/1995 |
| EP | 0692316 | 1/1996 |
| EP | 0707031 | 4/1996 |
| EP | 0719593 | 7/1996 |
| EP | 0 761 174 | 3/1997 |
| EP | 0 779 060 | 6/1997 |
| EP | 0801899 | 10/1997 |
| EP | 0826748 | 3/1998 |
| EP | 0867490 | 9/1998 |
| EP | 0928587 | 7/1999 |
| EP | 0928588 | 7/1999 |
| EP | 0928837 | 7/1999 |
| EP | 0936001 | 8/1999 |
| EP | 0966910 | 12/1999 |
| EP | 1001013 | 5/2000 |
| EP | 1006177 | 6/2000 |
| EP | 1031385 | 8/2000 |
| EP | 1083195 | 3/2001 |
| EP | 1084822 | 3/2001 |
| EP | 1123904 | 8/2001 |
| EP | 1132147 | 9/2001 |
| EP | 1197268 | 4/2002 |
| EP | 1221469 | 7/2002 |
| EP | 1224983 | 7/2002 |
| EP | 1245668 | 10/2002 |
| EP | 1253118 | 10/2002 |
| EP | 1331207 | 7/2003 |
| EP | 1334779 | 8/2003 |
| EP | 1398367 | 3/2004 |
| EP | 1452242 | 9/2004 |
| EP | 1464631 | 10/2004 |
| EP | 1479756 | 11/2004 |
| EP | 1493803 | 1/2005 |
| EP | 1518883 | 3/2005 |
| EP | 1518922 | 3/2005 |
| WO | WO8100972 | 4/1981 |
| WO | WO8101409 | 5/1981 |
| WO | WO8503243 | 8/1985 |
| WO | WO8706927 | 11/1987 |
| WO | WO8804529 | 6/1988 |
| WO | WO8909246 | 10/1989 |
| WO | WO9002774 | 3/1990 |
| WO | WO9003992 | 4/1990 |
| WO | WO9004001 | 4/1990 |
| WO | WO9008651 | 8/1990 |
| WO | WO9102773 | 3/1991 |
| WO | WO9103326 | 3/1991 |
| WO | WO9115610 | 10/1991 |
| WO | WO9203357 | 3/1992 |
| WO | WO9203358 | 3/1992 |
| WO | WO9210309 | 6/1992 |
| WO | WO9210549 | 6/1992 |
| WO | WO9220634 | 11/1992 |
| WO | WO9303919 | 3/1993 |
| WO | WO9307224 | 4/1993 |
| WO | WO9414904 | 7/1994 |
| WO | WO9426422 | 11/1994 |
| WO | WO9505748 | 3/1995 |
| WO | WO9511794 | 5/1995 |
| WO | WO9520253 | 7/1995 |
| WO | WO9521216 | 8/1995 |
| WO | WO9531584 | 11/1995 |
| WO | WO9602144 | 2/1996 |
| WO | WO9609362 | 3/1996 |
| WO | WO9613556 | 5/1996 |
| WO | WO9616526 | 5/1996 |
| WO | WO9623860 | 8/1996 |
| WO | WO9626671 | 9/1996 |
| WO | WO9637529 | 11/1996 |
| WO | WO9701599 | 1/1997 |
| WO | WO9703140 | 1/1997 |
| WO | WO9703141 | 1/1997 |
| WO | WO9706208 | 2/1997 |
| WO | WO9710289 | 3/1997 |
| WO | WO9713600 | 4/1997 |
| WO | WO9724469 | 7/1997 |
| WO | WO9739073 | 10/1997 |
| WO | WO9811159 | 3/1998 |
| WO | WO 98/18396 | 5/1998 |
| WO | WO9831197 | 7/1998 |
| WO | WO9838935 | 9/1998 |
| WO | WO9904665 | 2/1999 |
| WO | WO9912392 | 3/1999 |
| WO | WO9915019 | 4/1999 |
| WO | WO9918030 | 4/1999 |
| WO | WO9920723 | 4/1999 |
| WO | WO9920727 | 4/1999 |
| WO | WO9920807 | 4/1999 |
| WO | WO9927053 | 6/1999 |
| WO | WO9927054 | 6/1999 |
| WO | WO9927057 | 6/1999 |
| WO | WO9927058 | 6/1999 |
| WO | WO9929477 | 6/1999 |
| WO | WO9932234 | 7/1999 |
| WO | WO9937477 | 7/1999 |
| WO | WO9938642 | 8/1999 |
| WO | WO9951134 | 10/1999 |
| WO | WO9953251 | 10/1999 |
| WO | WO9955766 | 11/1999 |
| WO | WO9957205 | 11/1999 |
| WO | WO9961184 | 12/1999 |
| WO | WO9963972 | 12/1999 |
| WO | WO0006674 | 2/2000 |
| WO | WO0015180 | 3/2000 |
| WO | WO0016672 | 3/2000 |
| WO | WO0029538 | 5/2000 |
| WO | WO0041522 | 7/2000 |
| WO | WO0043324 | 7/2000 |
| WO | WO0047402 | 8/2000 |
| WO | WO0050545 | 8/2000 |
| WO | WO0050552 | 8/2000 |
| WO | WO0055288 | 9/2000 |
| WO | WO0056537 | 9/2000 |
| WO | WO0058389 | 10/2000 |
| WO | WO0069984 | 11/2000 |
| WO | WO0071651 | 11/2000 |
| WO | WO0073706 | 12/2000 |
| WO | WO0112090 | 2/2001 |
| WO | WO0118102 | 3/2001 |
| WO | WO0123274 | 4/2001 |
| WO | WO0123516 | 4/2001 |
| WO | WO0151096 | 7/2001 |
| WO | WO0160157 | 8/2001 |
| WO | WO0173431 | 10/2001 |
| WO | WO0179332 | 10/2001 |
| WO | WO0185827 | 11/2001 |
| WO | WO0186210 | 11/2001 |
| WO | WO0186289 | 11/2001 |
| WO | WO0189820 | 11/2001 |
| WO | WO0194477 | 12/2001 |
| WO | WO0202722 | 1/2002 |
| WO | WO0206436 | 1/2002 |
| WO | WO0206438 | 1/2002 |
| WO | WO0208370 | 1/2002 |
| WO | WO0208371 | 1/2002 |
| WO | WO0208373 | 1/2002 |
| WO | WO0214065 | 2/2002 |
| WO | WO0233038 | 4/2002 |

(56) References Cited

FOREIGN PATENT DOCUMENTS

| | | |
|---|---|---|
| WO | WO0242408 | 5/2002 |
| WO | WO02040628 | 5/2002 |
| WO | WO02072653 | 9/2002 |
| WO | WO02078862 | 10/2002 |
| WO | WO02078953 | 10/2002 |
| WO | WO02092747 | 11/2002 |
| WO | WO02096761 | 12/2002 |
| WO | WO03008528 | 1/2003 |
| WO | WO03011102 | 2/2003 |
| WO | WO03015588 | 2/2003 |
| WO | WO03018734 | 3/2003 |
| WO | WO03027218 | 4/2003 |
| WO | WO03038143 | 5/2003 |
| WO | WO03043480 | 5/2003 |
| WO | WO03043482 | 5/2003 |
| WO | WO03044834 | 5/2003 |
| WO | WO03051988 | 6/2003 |
| WO | WO03059992 | 7/2003 |
| WO | WO03062291 | 7/2003 |
| WO | WO03070828 | 8/2003 |
| WO | WO03090003 | 10/2003 |
| WO | WO03096863 | 11/2003 |
| WO | WO03096866 | 11/2003 |
| WO | WO03099096 | 12/2003 |
| WO | WO2004000082 | 12/2003 |
| WO | WO2004005394 | 1/2004 |
| WO | WO2004009691 | 1/2004 |
| WO | WO2004014139 | 2/2004 |
| WO | WO2004018607 | 3/2004 |
| WO | WO2004018611 | 3/2004 |
| WO | WO2004022669 | 3/2004 |
| WO | WO2004024025 | 3/2004 |
| WO | WO2004024348 | 3/2004 |
| WO | WO2004026921 | 4/2004 |
| WO | WO2004033301 | 4/2004 |
| WO | WO2004045783 | 6/2004 |
| WO | WO2004046301 | 6/2004 |
| WO | WO2004046302 | 6/2004 |
| WO | WO2004063241 | 7/2004 |
| WO | WO2004064572 | 8/2004 |
| WO | WO2004067588 | 8/2004 |
| WO | WO2004082445 | 9/2004 |
| WO | WO2004092283 | 10/2004 |
| WO | WO2004092450 | 10/2004 |
| WO | WO2004093622 | 11/2004 |
| WO | WO2004108816 | 12/2004 |
| WO | WO2004108842 | 12/2004 |

OTHER PUBLICATIONS

"Chemlon Black P2297 Material Safety Data Sheet" written by Akzo Nobel, printed on Apr. 20, 2005.
"The Remarkable Fluoropolymer Coating That Lasts 100 Times Longer Than Other Coatings" by Whitford Corporation, published prior to 2002.
"Utah Medical Products Inc. Specialized Dissection Electrodes" from http://www.utahmed.com/dissect.htm, 2000-2002, printed on Jun. 18, 2003.
Feb. 23, 2010 Final Office Action for U.S. Appl. No. 11/330,499.
Oct. 5, 2009 Office Action for U.S. Appl. No. 11/330,499.
Appellant's Appeal Brief from U.S. Appl. No. 11/330,499, filed Jul. 6, 2010.
Examiner's Answer from U.S. Appl. No. 11/330,499 mailed on Jul. 29, 2010.
Appellant's Reply Brief from U.S. Appl. No. 11/330,499, filed Aug. 20, 2010.
Decision on Appeal for U.S. Appl. No. 11/330,499 dated Apr. 26, 2012.

* cited by examiner

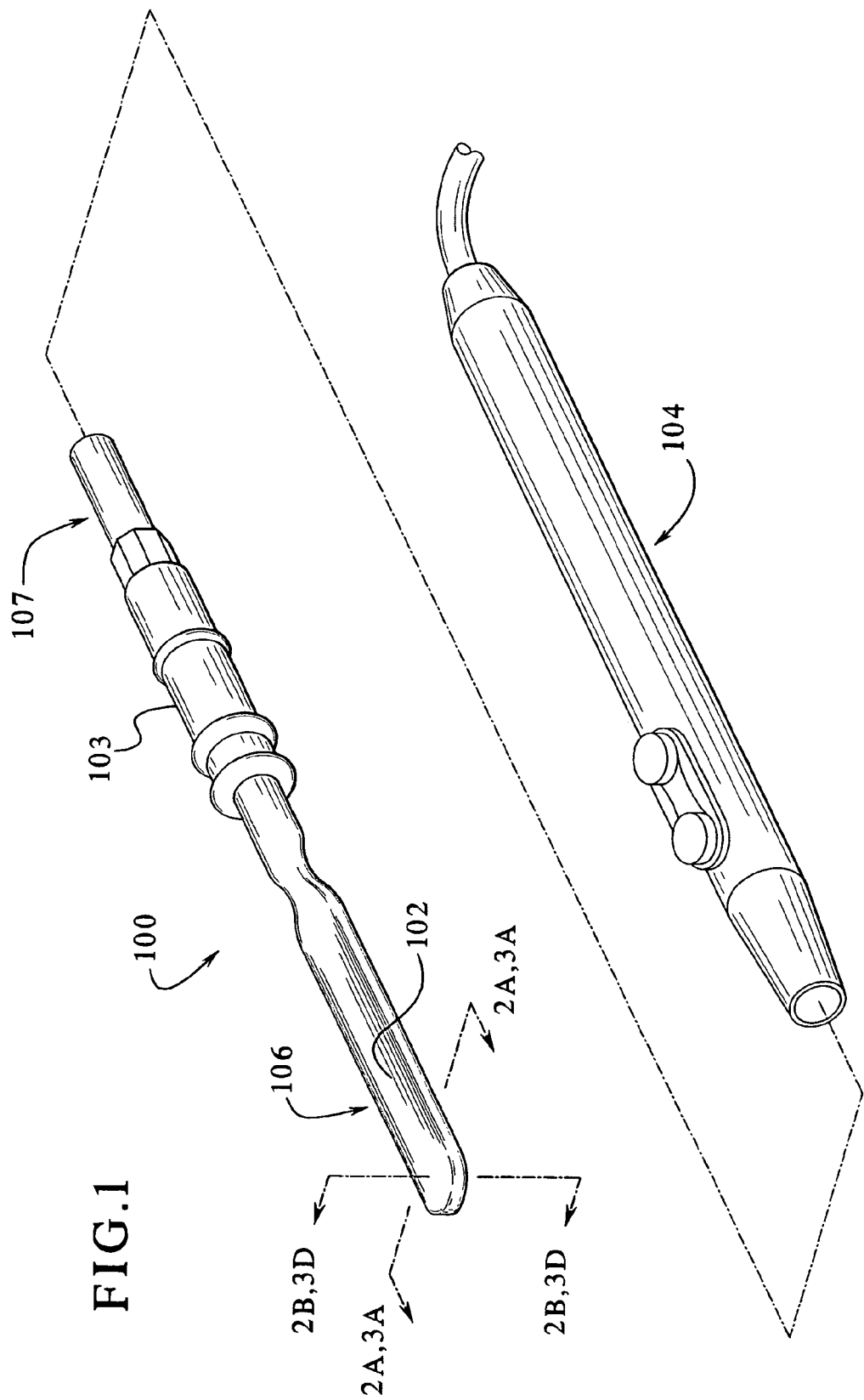

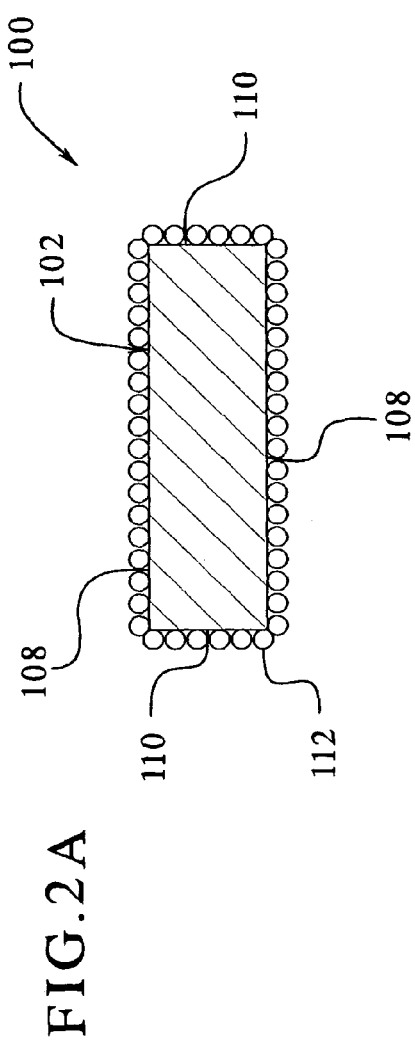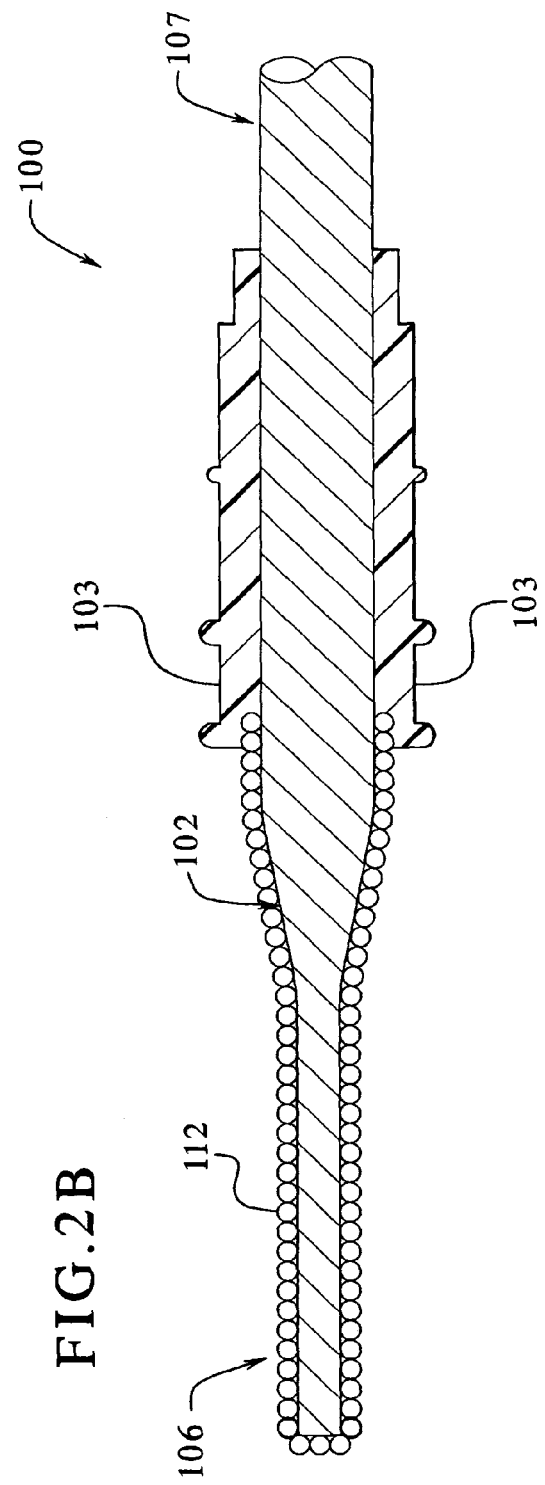
FIG.2A
FIG.2B

ELECTROSURGICAL ELECTRODE AND METHOD OF MANUFACTURING SAME

PRIORITY CLAIM

This application is a divisional of and claims the benefit of U.S. patent application Ser. No. 11/127,545, filed May 12, 2005, now U.S. Pat. No. 7,147,634, the entire contents are incorporated herein.

CROSS REFERENCE TO RELATED APPLICATIONS

This application relates to the following co-pending commonly owned patent applications: "ANTI-MICROBIAL ELECTROSURGICAL ELECTRODE AND METHOD OF MANUFACTURING SAME," Ser. No. 12/776,039, "ELECTROSURGICAL ELECTRODE AND METHOD OF MANUFACTURING SAME," Ser. No. 11/637,446, and "ELECTROSURGICAL ELECTRODE AND METHOD OF MANUFACTURING SAME," Ser. No. 11/330,499.

BACKGROUND

Electrosurgery refers to surgical procedures that pass high frequency, alternating electrical current through body tissues to cut or coagulate the tissues. Electrosurgical instruments or tools such as electrosurgical electrodes are used in these surgical operations to cut, coagulate and cauterize the tissue of a patient. The electrodes conduct the high frequency alternating electrical current from a generator to the patient to perform these operations. The generator is the source of the electricity for the surgical procedure. Because standard electrical current alternates at a frequency of sixty cycles per second (60 Hz), which could cause excessive neuromuscular stimulation and possibly electrocution if used, the generator takes sixty cycle current and increases the frequency to over 300,000 cycles per second (300,000 Hz). At this frequency, the electrical energy can pass through the patient with minimal neuromuscular stimulation and no risk of electrocution. Additionally, the generators are able to produce a variety of electrical waveforms. A constant waveform, which produces heat very rapidly, is generally used to vaporize or cut body tissue. An intermittent waveform produces less heat and is generally used to coagulate body tissue. Several different waveforms may used in an electrosurgical procedure to achieve different effects.

As described above, electrosurgical electrodes are used to cut or coagulate the body tissue in an electrosurgical procedure. Many sizes and shapes of electrosurgical electrodes such as blades, scalpels, needles, wire forms, balls and probes are available. Most electrosurgical electrodes are made of metal, typically stainless steel. Generally, a portion of the electrode is sheathed or encapsulated with an insulative material such as a plastic material. The electrodes are typically inserted into and connected to a handpiece for manipulating the electrode during surgery.

The working surface of the electrosurgical electrode or the exposed end of the electrode is not encapsulated with plastic or any type of electrically insulative material. The working surface generates heat and therefore is subject to high temperatures during use. The high temperature causes the body tissues to tend to stick to the working surface of the electrode. Specifically, the elevated temperature of the electrode causes charred tissue, commonly called "eschar," to adhere or stick to the working surface of the electrode. The buildup of tissue or eschar on the working surface of the electrode negatively affects the performance of the electrode during surgery. In particular, a buildup of tissue on the electrode reduces the transfer of energy to and from the electrode which decreases the cutting effectiveness of the electrode. Additionally, the tissue buildup may obscure the vision of the surgeon and therefore make it more difficult to perform the surgery.

As a result, efforts are made during surgery to keep the working surface of the electrode clean. Such cleaning methods include rubbing, brushing or scraping the electrode surface against a scouring pad or other suitable cleaning device. The continuous cleaning of the surface of the electrode, however, prolongs the surgical procedure which is not desirable. Therefore, the surgeon is left with the options of replacing the electrode during surgery, accepting reduced performance of the electrode, or expending valuable time and energy in an attempt to thoroughly clean the surface of the electrode with an abrasive pad. If the surgeon must clean the surface of the electrode with an abrasive pad, as while scouring the coated surface of the blade, the surgeon must spend additional time and attention to not damage or wear through the protective coating.

One method used to solve the problem of tissue or eschar buildup on the surface of the electrode is to coat the surface of the electrode with a non-stick or surface release coating. The non-stick or release coating minimizes the sticking or adherence of the tissue on the surface of the electrode and enables the built up tissue to be removed more easily and efficiently from the surface.

Several different types of non-stick coatings have been used or suggested for application to electrosurgical electrodes. Some of the different non-stick coatings or materials include fluorinated hydrocarbon materials, polytetrafluoroethylene, perfluoro-alkoxy, flexible silicone elastomers, ceramic composites, paralyene silane polymers and other suitable non-stick coatings. Different methods exist for applying the non-stick coating to the surface of the electrosurgical electrodes. However, the non-stick or release coatings have varying degrees of electrically insulative qualities, and therefore, may change and/or impair the electrical conductivity of the surface of the electrodes. Some of such coatings are thinner (due to their inherent technical limitations and/or cost of production reasons) and thus posses less than optimum electrical and/or insulative properties. Other coatings provide discontinuous protection of the underlying metal blade and may contain micro fractures, holes and/or "holidays." It should be appreciated that coating areas of reduced thickness and areas wherein the coating is missing may alter the electrical insulative or surface characteristics of the electrical energy emitted from the surface of the coating, thus affecting the quality and consistency of the use of the blade. Such altered electrical insulative properties present an erratic and potential inconsistent function of the use of the electrosurgical device as a surgical tool.

Moreover, certain of these non-stick coatings, particularly the fluoropolymers, may break down and emit harmful byproducts as the coated portion or portions of the electrosurgical electrode are heated to temperatures above 500° F. (260° C.). In addition to breaking down at temperatures above 500° F. (260° C.), as certain of these non-stick coatings approach 500° F. (260° C.), micro-fractures or fissures in the coating surface take place. These micro-fractures provide additional areas for eschar or carbonized organic matter to adhere to the electrosurgical device. As the coating breaks down due to thermal overheating of specific areas of the blade, particularly the edges and tip of the blade, the electrical insulative quality of the original coating is diminished and eventually destroyed. Accordingly, the user will need to change the electrical settings of the electrical generator or need to change to a new blade to achieve consistent end use results.

Another issue associated with surgical instruments such as electrosurgical electrodes is the cleanliness of the working surface and other surfaces of the electrode as the electrode contacts tissue and other parts of the body. The tissue or eschar buildup on the working surface of the electrode creates an environment where bacteria and other harmful organisms may cultivate and be introduced into the body during the surgical process. Furthermore, any gaps between the plastic sheath and the electrode or any fractures, fissures or other defects in the plastic sheath enables bacteria and other organisms to get underneath the plastic sheath and also into and grow in the fractures, fissures and defects or other interstices in the plastic sheath. This warm environment also promotes organism and bacteria growth. This further promotes the growth of the bacteria and the harmful organisms which may migrate to the surface of the electrode or to the patient. Bacteria forming on the eschar which in turn enters a patient's body during a surgical procedure can cause significant difficulties and complications for the patient after the surgical procedure is complete. As a result, minimizing the buildup of tissue or eschar and thus minimizing the growth of bacteria and other organisms on the electrode surface (and between the insulating sheath and the electrode shaft) is desirable to enable the electrode to be used multiple times to minimize and/or prevent infections or other related complications from developing in a patient following surgery.

Accordingly, there is a need for an improved electrosurgical device such as a single use or multi-use electrosurgical electrode and method of manufacturing same which minimizes the buildup of tissue on the substrate or working surface of the electrode during storage, use or pauses in the use of the electrode. Additionally, there is a need for an improved electrosurgical device which has superior easy-to-clean characteristics if the user desires to or must clean the electrosurgical device for multiple uses and/or store the previously used blades for future uses.

SUMMARY

The present disclosure relates in general to an electrosurgical electrode, and, specifically, to an electrosurgical electrode coated with a specifically formulated epoxy modified rigid silicone powder non-stick coating and a method of manufacturing the same.

In one embodiment, an epoxy modified rigid silicone powder non-stick coating is applied to an electrosurgical device such as an electrosurgical blade, knife, wire, ball or other shape. In one embodiment, the electrosurgical device includes an electrode including a conductive substrate or conductive material where at least a portion of the electrode is encapsulated in a substantially electrically insulative material such as plastic, a handle connected to one end of the electrode and electrical conductors which are attached inside the handle to conduct electricity from an electrical source and deliver or transfer the electricity to the electrode. In one embodiment, the electrode conducts electricity to generate heat and cut, coagulate and/or cauterize tissue during a surgical procedure.

In one embodiment, the epoxy modified rigid silicone powder coating is applied uniformly and evenly to the surface or surfaces of the electrode to completely coat the exposed distal end or portion and a portion of the plastic encapsulated portion of the electrosurgical device. The epoxy modified rigid silicone powder has both high temperature capabilities and non-stick properties. The high temperature resistance of the epoxy modified rigid silicone powder enables the electrosurgical electrode to be heated to temperatures above which other non-stick coatings may break down and emit harmful byproducts. Accordingly, after multiple uses, the epoxy modified rigid silicone powder coating retains its hardness, surface toughness and non-stick properties on the electrode and the buildup of tissue or eschar on the working surface of the electrode is reduced or prevented.

In one embodiment, the electrosurgical device is coated with a silicone powder coating that is modified with an epoxy, which when applied to the electrosurgical device, forms a rigid or relatively hard silicone non-stick coating. In one embodiment, the epoxy modified rigid silicone powder coating includes a solid silicone resin and a polysiloxane additive. The silicone resin may be selected from the group including a phenyl polysiloxane powder resin, a methyl polysiloxane powder resin, a methyl phenyl siloxane powder resin, a phenyl silicone powder, a methyl phenyl silicone and a phenyl alkyl polysiloxane powder resin. The siloxane additive may be selected from the group including a methyl alkyl polysiloxane, a dimethyl polysiloxane and a methyl phenyl siloxane. It should be appreciated that any suitable epoxy or organic resin base combined with a suitable silicone powder with high temperature capabilities and non-stick properties (and possibly further modified with suitable organic materials and resins) may be implemented to advance or improve the end use high temperature and non-stick properties of the disclosed powder coating technology.

In one embodiment, the epoxy modified rigid silicone powder particles in the coating enable the electrosurgical device to reach a desired temperature quicker than conventional electrosurgical devices because the formulation of the rigid epoxy/silicone powder coating can be formulated with special pigments and additives to increase the thermal conductivity of the coated electrode surface compared to conventional PTFE or elastomeric silicone coated electrode surfaces. As a result, electricity or heat is more effectively controlled and efficiently conducted or transferred to the electrode surface. Moreover, compared to elastomeric silicone coatings, in one embodiment, the epoxy modified rigid silicone powder may be ground to a finer mesh size for purposes of applying a thinner coating, thereby improving the thermal conductivity and coating flexibility without resulting in pinholes or fissures in the coating. In another embodiment, a thicker coating of the epoxy modified rigid silicone powder is applied to the electrosurgical device. Depending on the specific end use characteristics desired, such a thicker coating may be achieved by either formulating and manufacturing different particle sizes of the powder coating or through suitable coating application techniques.

In one aspect of this embodiment, the amount and density of the epoxy modified rigid silicone powder particles (and additives, if any, used in a particular formulation) applied to the surfaces of the electrode is increased or decreased based on the desired electrical and heat conductivity of the electrosurgical device. The electrical and thermal conductivity can be altered when more epoxy modified rigid silicone powder particles are included in the coating, when less epoxy modified rigid silicone powder particles are included in the coating or when special pigments or additives are used to enhance one or more specific characteristics to further optimize the desired end use of the device. Additionally, the density and particle size of the epoxy modified rigid silicone powder particles applied to the surface of the electrode may be adjusted to increase or decrease the electrical conductivity. When the electrical conductivity of the electrode is increased, the temperature of the surface of the electrode is changed. This enables the coating mixture to be adjusted to optimize the desired end use of the device.

It should be appreciated that one or more combinations of different shaped epoxy modified rigid silicone powder particles may be used on the working surface of the electrosurgical electrode. Additionally, the density or thickness ranges of the epoxy modified rigid silicone powder particles may vary depending on the design specifications of an end product or final product. The density or distribution of the epoxy modified rigid silicone powder particles may vary from covering or adhering to approximately ten percent of the surface of the electrosurgical electrode to approximately sixty percent or more of the surface. Similarly, the density of the epoxy modified rigid silicone powder particles may vary depending on the end use criteria.

In another embodiment, one or more additional epoxy modified rigid silicone powder layers are applied to the first or primary epoxy modified rigid silicone powder layer applied to the surface of the electrosurgical device to meet specific design specifications or coating requirements of a manufacturer. The additional bonding material layers may be the same or different than the first epoxy modified rigid silicone powder layer and are applied to the first rigid silicone powder layer until a predetermined thickness is achieved. Additionally, different materials may be added to the bonding material layer or layers, based on specific design specifications. In another embodiment, different liquid bonding agents may be introduced to the top of the first layer of the epoxy modified rigid silicone powder before a second layer of the epoxy modified rigid silicone powder is attached to the first layer. This process may be repeated to build thicker layers of epoxy modified rigid silicone powder on all or a selective or individual portion of an electrosurgical device.

In one embodiment, prior to applying the epoxy modified rigid silicone powder to one or more surfaces of the electrosurgical device, the electrosurgical electrode is positioned on a support. Initially, the surface of the electrosurgical electrode is cleaned with a cleaner to remove impurities which may be present on the surface of the electrosurgical electrode. The cleaner such as a solvent may be manually applied or mechanically applied to the electrosurgical electrode. In one embodiment, grit blasting or sandblasting is used to clean the surface of the electrosurgical electrode. Alternatively, the electrosurgical electrode may be pre-cleaned or the method may be performed in a "clean room" where the cleaned part is manufactured and the step is not necessary. In another embodiment, the electrode is heated to a temperature, depending on the metal alloy of the electrode, in excess of 700° F. (371° C.) for a period of time sufficient to thermally degrade surface impurities. In another embodiment, the electrosurgical device may be cleaned in a batch or bulk cleaning method, thereby cleaning all of the surfaces of the electrosurgical device.

In one embodiment, the epoxy modified rigid silicone powder has self-adhesive properties. In this embodiment, when applied to the surfaces of the electrosurgical device, the epoxy modified rigid silicone powder particles will adhere. Thus, in this embodiment, no bonding layer is necessary to be applied to the electrode.

In another embodiment, the epoxy modified rigid silicone powder particles must be affixed to one or more surfaces of the electrosurgical device using one or more wet bonding materials. In this embodiment, after the surface of the electrosurgical electrode is cleaned, a layer of a wet bonding material such as a primer is applied to one or more surfaces of the electrosurgical device. The layer of wet bonding material is preferably applied uniformly so as to avoid forming a thick layer, which is thicker than what is necessary or required, and avoid drippings which may detract from the bonding ability to the electrosurgical device.

In one embodiment, the bonding material layer may be formulated to improve the bonding capabilities of the subsequent epoxy modified rigid silicone powder coating layer or layers applied to the surface of the electrosurgical electrode. In this embodiment, the wet bonding material may include one or more additives which change or enhance one or more characteristics of the wet bonding material. For example, in one embodiment, the wet bonding material includes an ultraviolet light cure resin to semi or fully cure the bonding layer. In another embodiment, the wet bonding material includes an electron beam cure resin. It should also be appreciated that the bonding material may be any suitable bonding material or agent. For example, a thin layer of any suitable epoxy may be utilized as the bonding layer to coat the surface of the electrode prior to the application of the epoxy modified rigid silicone powder.

In one embodiment, while the bonding material layer is still wet, a single layer of epoxy modified rigid silicone powder is sprayed over the wet bonding material. In one embodiment, a substantially uniform layer of epoxy modified rigid silicone powder is applied to the wet bonding material. The epoxy modified rigid silicone powder particles adhere to the wet surface area of the bonding material in an even manner. In this embodiment, when the wet bonding material is completely coated with one layer of the uniform epoxy modified rigid silicone powder mixture of particles, additional epoxy modified rigid silicone powder particles cannot stick to the bonding material layer because the insulative qualities of the adhered epoxy modified rigid silicone powder particles attached to the bonding material layer act as a barrier to other particles attaching to the wet bonding material layer. Therefore, the epoxy modified rigid silicone powder particles do not build up or form an uneven surface area on the surface of the electrosurgical electrode. Additionally, the wet bonding material layer may be a thick layer where the uniform epoxy modified rigid silicone powder particles sink into and are completely covered by the wet bonding material layer. In another embodiment, the wet bonding material layer is a substantially thin layer on the surface of the electrosurgical device and a substantial portion of the epoxy modified rigid silicone powder particles are exposed on the wet bonding material layer.

In another embodiment, an electrostatic, tribo-charged or opposite electrostatic charged powder spray method is used to apply the epoxy modified rigid silicone powder particles to either a dry electrosurgical device or an electrostatic device coated with the wet bonding adhesion promoting material. In one embodiment, the wet bonding agent is from the epoxy resin family. The electrostatically charged particle powder spray enables an operator to better control the application uniformity of the epoxy modified rigid silicone powder particles and thereby enhance the uniformity, density and application of the epoxy modified rigid silicone powder particles to the wet bonding material on the electrosurgical device. It should be appreciated that the epoxy modified rigid silicone powder particles may have one or more surface characteristics altered to allow for more efficient electrostatic, tribocharged or opposite electrostatic charged powder spray techniques to be used to apply the epoxy modified rigid silicone powder particles to an electrosurgical device.

Moreover, the above-described "tribo-charge" application technique alters the edge coverage thickness of the applied powder based on any design requirements which require a more uniformly applied epoxy modified silicone nonstick powder to all surfaces of the device, whether the configuration has sharp or round edges. This technique results in optimizing the different edge coverage thicknesses of the applied epoxy modified rigid silicone powder, whether the electrosurgical device is a blade, ball, wire or a different shape.

It should be appreciated that an electrosurgical device manufactured with an epoxy modified rigid silicone powder coating exhibits improved uniformity of coating thickness and coverage of the critical edge or tip characteristics. In one embodiment, due at least in part to the "Farraday" effect of applying increased amounts of coatings to a sharp corner or edge, electrostatically applied epoxy modified rigid silicone powder particles are more easily applied to and attach to the thin or sharp edges of the electrosurgical device. In this embodiment, by altering the electrostatic powder coating equipment or techniques of application, such as by changing the power settings, waveforms and/or other electrical characteristics of the application equipment, the edges of the electrosurgical device are selectively more or less heavily coated with the epoxy modified rigid silicone powder.

After the epoxy modified rigid silicone powder coatings are applied to the surfaces of the electrode, the coatings are cured in a suitable device, such as an oven or furnace, or by using a suitable curing method or process. The curing process hardens the coatings and promotes the adherence of the coatings to the electrode. The coated electrode, therefore, minimizes the build up of eschar on the surfaces of the coated electrosurgical device.

In one embodiment, in addition to the epoxy modified rigid silicone powder particles, a plurality of anti-microbial particles such as silver, silver ceramic, silver oxide or silver compounds or any suitably anti-microbial agent are applied to one or more of the surfaces of the electrosurgical device to reduce and kill bacteria and other potential germs that may be located on the surface(s) of the electrosurgical device. In one aspect of this embodiment, the anti-microbial particles are interspersed with the epoxy modified rigid silicone powder particles and a layer of anti-microbial material is applied to the electrosurgical device along with the epoxy modified rigid silicone powder particles. The above process can be repeated as necessary to maintain the effectiveness of the anti-microbial surface. The addition of the anti-microbial material tends to kill bacteria or other harmful organisms that contact the surface of the electrode during and after the surgical procedure. This coated electrode may be used multiple times in different surgical procedures without requiring sterilization (even though sterilization is preferred) because the anti-microbial particles are capable of killing the bacteria and other harmful organisms which contact the surfaces of the electrode. The coated electrosurgical device therefore minimizes or reduces the chance of infections or other complications in the body after the surgical procedure is complete.

It is therefore an advantage of the present apparatus and method to provide an epoxy modified rigid silicone powder coating to the surface of an electrosurgical device to prevent the build up of tissue on the device.

A further advantage of the present apparatus and method is to provide an epoxy modified rigid silicone powder coating to the surface of an electrosurgical device to enable the device to be used multiple times in different surgical procedures.

Another advantage of the present apparatus and method is to provide an electrosurgical device that is coated with a epoxy modified rigid silicone powder to enable the device to be heated to temperatures at which other non-stick coatings break down and lose their non-stick properties, wherein in the process of decomposing, such other non-stick coatings generate toxic and noxious gasses and harmful airborne particles.

Another advantage of the present apparatus and method is to provide an electrosurgical device coated with a powder coating which includes a silicone resin and siloxane additive without any fluoropolymers.

Additional features and advantages of the present apparatus and method are described in and will be apparent from, the following Detailed Description and the Figures.

BRIEF DESCRIPTION OF THE FIGURES

The patent or application file contains at least one drawing executed in color. Copies of this patent or patent application publication with color drawing(s) will be provided by the U.S. Patent and Trademark Office upon request and payment of the necessary fee.

FIG. 1 is a front perspective view of one embodiment of a coated electrosurgical instrument.

FIG. 2A is a cross-section view of the embodiment of FIG. 1 taken generally along the line 2A-2A.

FIG. 2B is a cross-section view of the embodiment of FIG. 1 taken generally along the line 2B-2B.

DETAILED DESCRIPTION

Figure 3A:
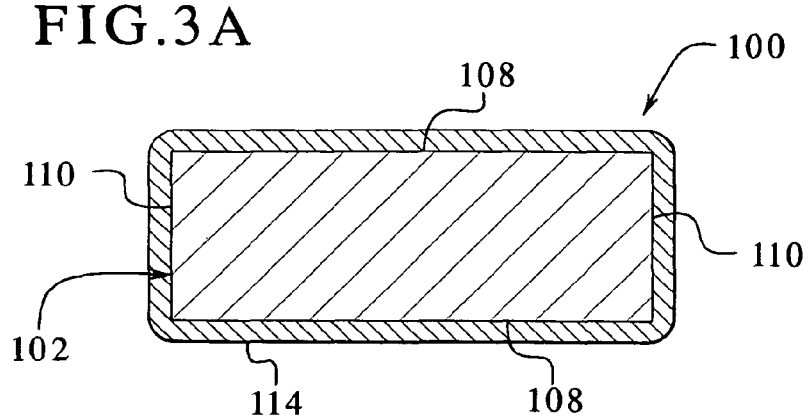
FIG. 3A is a cross-section view of another embodiment of the electrosurgical instrument of FIG. 1 taken generally along the line 3A-3A where a primer or base coating is applied to the surfaces of the instrument.

Referring now to FIG. 1, one embodiment is illustrated where a coating of epoxy modified rigid silicone powder is applied to an electrosurgical device such as an electrosurgical instrument, blade or knife 100. In this embodiment, the coated electrosurgical instrument 100 includes an electrode 102 and a holding device such as handle 104 or other suitable holding device which is connected to the electrode 102 and enables the electrode to be manipulated in a surgical procedure. The electrode includes a conductive substrate or conductive material which enables the electrode to conduct electrical energy or electricity. In one embodiment, a portion of the electrode 102 is coated, encapsulated or over-molded with an electrically insulative material 103 such as a suitable plastic. The coated electrode 102 includes a distal end or working end 106 and a proximal end or connection end 107 which may be bare metal and is not coated with any coating material. The exposed distal end 106 of the electrode is used to cut, coagulate and/or cauterize tissue in a body during a surgical procedure. Specifically, electrical energy such as electricity is transferred from a suitable electrical source through suitable wiring to electrical conductors (not shown) inside the handle 104. The electrical energy is then transferred from the conductors (not shown) in the handle 104 to the proximal end 107 of the electrode 102, which is electrically connected to the conductors in the handle, and energizes the electrode 102.

Once energized, the electrical and thermal energy produced by the electrically charged electrode generates an elevated temperature which enables the distal end 106 of the electrode to cut, coagulate and/or cauterize tissue in a body.

In one embodiment, an epoxy modified rigid silicone powder coating is evenly applied to the entire surface of the electrode to minimize the buildup of tissue or eschar on the working surface of the electrode. The epoxy modified rigid silicone powder coating has high temperature capabilities (i.e., a melting temperature of approximately 900° F. (482° C.)) and non-stick properties such that the electrosurgical electrode may be heated to temperatures above which other non-stick coatings may break down and emit harmful byproducts. Accordingly, the rigid silicone coating minimizes the buildup of tissue or eschar on the surface of the electrode by minimizing the adherence of the tissue on the surface of the electrode. Specifically, the epoxy modified rigid silicone powder coating forms a non-stick surface which reduces or prevents eschar from adhering to the surface coated with the epoxy modified rigid silicone powder. This enables a user such as a surgeon to continue a surgical procedure without having to continuously clean, scrape or brush off adhered charred tissue from the surface of the electrode.

In one embodiment, the epoxy modified rigid silicone powder coating includes a silicone resin and a polysiloxane additive. The silicone resins may be selected from the group including a phenyl polysiloxane powder resin, a methyl polysiloxane powder resin, a methyl phenyl polysiloxane powder resin, a phenyl alkyl polysiloxane powder resin, a methyl phenyl polysiloxane powder resin, a phenyl silicone powder and a methyl phenyl silicone. The siloxane additive includes a polysiloxane additive selected from the group consisting of a methyl alkyl polysiloxane, a dimethyl polysiloxane and a methyl phenyl siloxane. It should be appreciated that any suitable epoxy modified rigid silicone powder with high temperature capabilities and non-stick properties may be implemented.

In one embodiment, the polysiloxane additive is between about 0.5% to about 10% parts per weight of the powder coating. In one embodiment, the silicone resin is from about 5% to 75% parts per weight of the powder coating. In another embodiment, the powder coating includes epoxy cresol novolac. In this embodiment, the epoxy cresol novolac is from about 1% to about 50% parts per weight of the powder coating. In another embodiment, the powder coating includes o-cresol novolac. In this embodiment, the o-cresol novolac is from about 1% to about 40% parts per weight of the powder coating. In another embodiment, the powder coating includes a solid bisphenol-A/epichlorohydrin epoxy resin. In this embodiment, solid bisphenol-A/epichlorohydrin epoxy resin is from about 1% to about 50% parts per weight of the powder coating.

As the properly formulated and/or reformulated epoxy modified rigid silicone coating has an optimized or altered electrical conductivity, the epoxy modified rigid silicone powder particles applied to the surface of the electrode more evenly distributes the temperature and electrical energy transferred to the electrode while increasing the electrical conductivity of the electrode. The increase and relatively even distribution of electrical energy or electricity to the electrode enables the electrode to minimize "hot spots" or portions of the electrode which have a higher temperature due a disproportionate or non-uniform distribution of the electrical energy to the electrode. As a result, a surgeon can make more precise cuts or coagulate or cauterize discrete or specific parts of the tissue in the body with more accuracy. This improves the surgical procedure and also minimizes the time of the surgical procedure. The amount of or density of the epoxy modified rigid silicone powder particles or compounds included in the coating can be adjusted to increase or decrease the conductivity of the coating applied to the surface of the electrode. In another embodiment, electrically conductive pigments may be blended into the formulation to further enhance electrical energy transmission from the electrode thru the rigid silicone coating.

In one embodiment, the size of the epoxy modified rigid silicone powder particles may be changed as desired to accommodate different technical and coating requirements or specifications. In one embodiment, the epoxy modified rigid silicone powder particles include at least one relatively large particle and at least one relatively small particle. In another embodiment, the epoxy modified rigid silicone powder particles range in size such as from a sub-micron to approximately 125-150 microns the epoxy modified rigid silicone particle layers are substantially spherical particles, which creates a softer, less abrasive surface on the electrosurgical device.

In another embodiment, the uniform particle layer includes different sized epoxy modified rigid silicone powder particles applied to the surface of the electrosurgical device. In one example, hard abrasion resistant larger size particles and smaller electrically conductive particles are applied to create an abrasion resistant and electrically conductive surface of the electrosurgical device. It should be appreciated that any suitably sized and shaped epoxy modified rigid silicone powder particles may be applied to the surface of the substrate.

In one embodiment, prior to applying the epoxy modified rigid silicone powder to one or more surfaces of the electrosurgical device, the electrosurgical electrode is positioned on a support. Initially, the surface of the electrosurgical electrode is cleaned with a cleaner to remove impurities which may be present on the surface of the electrosurgical electrode. The cleaner such as a solvent may be manually applied or mechanically applied to the electrosurgical electrode. In one embodiment, grit blasting or sandblasting is used to clean the surface of the electrosurgical electrode. In one alternative embodiment, rather than grit blasting, an ultrasonic liquid cleaner is used to clean the electrosurgical electrode. In this embodiment, the ultrasonic liquid cleaner strips a microscopic layer off the top surface of the electrode. In another embodiment, the electrosurgical electrode may be thermally cleaned by heating the electrode to a temperature, depending on the metal alloy of the electrode, in excess of 700° F. (371° C.) for a period of time sufficient to thermally degrade surface impurities. In another alternative embodiment, the electrosurgical electrode may be pre-cleaned or the method may be performed in a "clean room" where the cleaned part is manufactured and this cleaning step is not necessary. In another embodiment, the electrosurgical device may be cleaned in a batch or bulk cleaning method, thereby cleaning all of the surfaces of the electrosurgical device.

In one embodiment, the epoxy modified silicone powder coating mixture formulation has self-adhesive properties. In this embodiment, when applied to the surfaces of the electrosurgical device, the epoxy modified rigid silicone powder particles will adhere. Thus, in this embodiment, no bonding layer is necessary to be applied to the electrode after the electrode is cleaned. In another embodiment, a silane coupling agent which is only a few molecules thick is used prior to the application of the epoxy modified rigid silicone powder. In this embodiment, the silane coupling or adhesion promoting agent remains wet on the electrode surface, the dry epoxy modified rigid silicone powder is applied directly to it and the electrode is cured once. One or more suitable powder topcoats may then be applied to the cured electrode, with or without suitable liquid coupling or bonding agents.

In one embodiment, a very thin liquid epoxy-based material is applied to the electrosurgical device after the electrode surface is cleaned but prior to the application of the epoxy modified rigid silicone powder particles. In another embodiment, prior to the application of the epoxy modified rigid silicone powder particles, a very thin liquid epoxy-based material is applied to the cleaned electrode surface and the electrode surface is semi-dried or semi-cured. These embodiments provide increased adhesion of the epoxy modified rigid silicone powder particles to the electrosurgical device by creating a linking or bonding agent between the electrosurgical device and the subsequently applied epoxy modified rigid silicone powder particles.

In another embodiment, the epoxy modified rigid silicone powder particles must be affixed to one or more surfaces of the electrosurgical device using one or more bonding materials. In this embodiment, after the electrosurgical device is cleaned or is clean, a layer of a substantially wet bonding material is applied to the electrosurgical device. The bonding material provides a wet or moist surface for the subsequent substantially uniform rigid silicone particle layer to adhere to. The wet bonding material may be any suitable bonding material, which meets the specific design specifications of the particular electrosurgical device. In one embodiment, it is important that the bonding material remain wet prior to the application of the rigid silicone particle layer so that the epoxy modified rigid silicone powder particles stick to or adhere to the wet bonding material. In this embodiment, a single layer of substantially uniform epoxy modified rigid silicone powder particles are applied or powder sprayed onto the wet bonding material layer until the wet bonding material layer is completely coated with the dry uniform particles and a desired thickness is achieved. The thickness of the coatings or coating layers is dependent on the specifications for the particular product, the amount of bonding material applied and the size and shape of the epoxy modified rigid silicone powder particles. It should be further appreciated that the epoxy modified rigid silicone powder particles may be applied to the electrosurgical device utilizing any of the processes described in published U.S. patent application No. 2004/0116792 which is incorporated herein by reference.

In one embodiment, the epoxy modified rigid silicone powder particles are sprayed or applied onto the wet bonding material as a single substantially uniform and substantially even layer which adheres to the sticky or wet surface of the bonding material. In another embodiment, the electrosurgical device is electrically grounded using a suitable grounding method. Grounding the electrosurgical device thereby grounds the wet bonding material layer, which is formulated to include solvents and/or liquids that conduct electrical energy. The substantially uniform epoxy modified rigid silicone powder particle layer has or will have an opposite electrical charge to that of the bonding material layer and therefore is electrically or electrostatically attracted to the wet bonding material layer as the epoxy modified rigid silicone powder particles are applied to that layer. In a further embodiment, an applicator such as a sifter or electrostatic fluidized bed is used to uniformly apply the epoxy modified rigid silicone powder particles to the wet bonding material layer. The sifter is similar to a conventional flour sifter or a drum sifter and is used in certain applications depending on the required application of the uniform particles. The electrostatic fluidized bed contains a porous membrane made of porous polyethylene or any suitable electrically non-conductive material which allows the aeration of the powder with pressurized air that is charged to approximately 60,000 volts with a metal grid under the porous membrane, thereby charging the epoxy modified rigid silicone powder particles. Charging the epoxy modified rigid silicone powder particles cause the particle to adhere to the grounded electrosurgical device placed above or in the fluidized bed.

After the substantially uniform epoxy modified rigid silicone particle layer is applied to the bonding material layer, the layer is cured to strengthen the bond between the uniform rigid silicone particle layer and the wet primer layer on the surface of electrosurgical device. The curing process may be performed by heating the layers at a predetermined temperature or temperatures, air-drying the layers or by utilizing any suitable internal or external curing process. When the substantially uniform epoxy modified rigid silicone powder particle layer has completed adhered or bonded to the bonding material layer, a suitable coating layer may be applied to the uniform epoxy modified rigid silicone powder particle layer. In this embodiment, the epoxy modified rigid silicone powder coating may be undercured in an oven or suitable device, thus creating a semi-cured layer to which subsequent liquid or epoxy modified rigid silicone powder layers may be attached with a final cure which will consolidate the multiple layers. The coating may be any suitable coating such as a topcoat or final coat material. Examples include corrosive or abrasive resistant coatings, non-stick coatings or low friction coatings, anti-microbial coatings and electrically insulative or conductive coatings or combinations thereof. It should be appreciated that areas of the electrosurgical device in which epoxy modified rigid silicone powder is not required can be vacuumed or mechanically wiped from the electrosurgical device prior to the oven curing of the coating. This saves much production time and further reduces production costs.

In one embodiment, the metal electrosurgical blade or device is heated to a temperature in excess of 500° F. (260° C.) using induction heating or other suitable heating methods. A portion of the electrosurgical device that is to be powder coated is immersed into a non-electrostatic fluidized bed up to the point where the coating is not required and held there for a period of time between one half second to approximately 10 seconds. A layer of epoxy modified rigid silicone powder particles will adhere to the portion of the electrosurgical device that has been immersed into the fluidized bed of the powder. The electrosurgical blade or device is then placed into a fixture or onto a conveyor device and passed through a heating chamber to finish cure the layer of epoxy modified rigid silicone powder particles. It should be appreciated that this technique reduces the amount of masking or fixturing required for powder spraying the same type of parts, particularly if the parts have complex shapes and/or blind cavities or recesses.

FIGS. 2A and 2B illustrate one embodiment of the electrosurgical blade 100 of FIG. 1 wherein a single even layer of epoxy modified rigid silicone powder particles 112 with self-adhesive properties is applied directly to the surface of the electrode 102 without the use of any bonding material layer. The electrode 102 includes major surfaces 108 and minor surfaces 110. The rigid silicone particle coating is uniformly and evenly applied to the major surfaces 108 and minor surfaces 110 of the electrode as shown in FIG. 2A. In this embodiment, the rigid silicone coating enables the electricity to be evenly conducted and displaced across the surfaces of the electrode. This provides substantial benefits in a surgical process by minimizing the buildup of tissue or eschar on the surface of the electrode thus reducing surgical time and possibly minimizing the likelihood of complications arising during surgery.

Figure 3B:
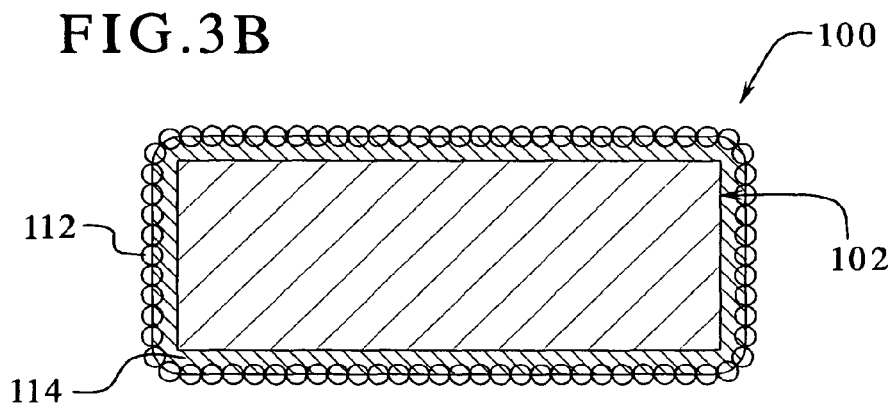
FIG. 3B is a cross-section view illustrating the embodiment of FIG. 3A, including a layer of epoxy modified rigid silicone powder particles.
Figure 3C:
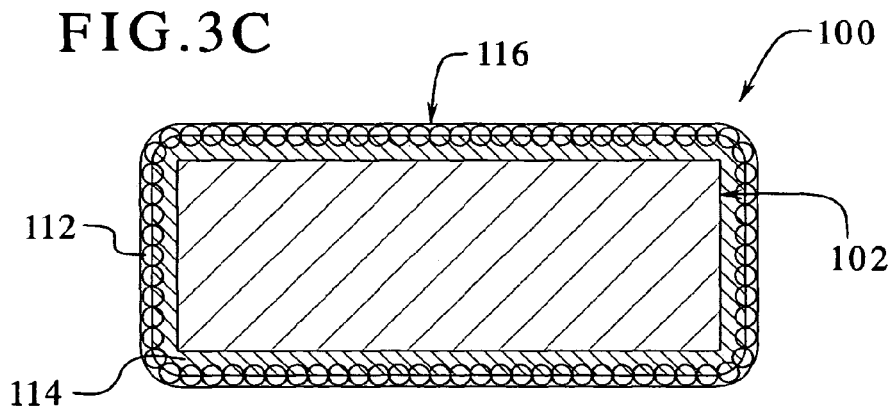
FIG. 3C is a cross-section view of FIG. 3B, including a top coating applied to the layer of epoxy modified rigid silicone powder particles.

FIGS. 3A, 3B and 3C illustrate another embodiment of the electrosurgical blade 100 of FIG. 1 wherein a single even layer of epoxy modified rigid silicone powder particles 112 is applied to the surface of the electrode 102 with the use of any suitable bonding material layer 114. In this embodiment the major surfaces 108 and minor surfaces 110 of the electrode are initially roughened to promote the adherence of the coatings to the surfaces. After the surfaces are roughened or suitably cleaned, a wet bonding material such as a primer 114 is applied to the major surfaces 108 and minor surfaces 110 of the electrode. The wet bonding material is applied evenly and uniformly to the surface of the electrode. While the wet bonding material is still substantially wet, a plurality of epoxy modified rigid silicone powder particles 112 are applied to the wet bonding material 114 as shown in FIG. 3B and as disclosed above. The dry epoxy modified rigid silicone powder particles engage, adhere to and are at least partially embedded in the wet bonding material 114. The wet bonding material 114 therefore causes the epoxy modified rigid silicone powder particles 112 to adhere to and enhance the adhesion of the epoxy modified rigid silicone powder particles to the surface of the electrode 102.

Figure 3D:
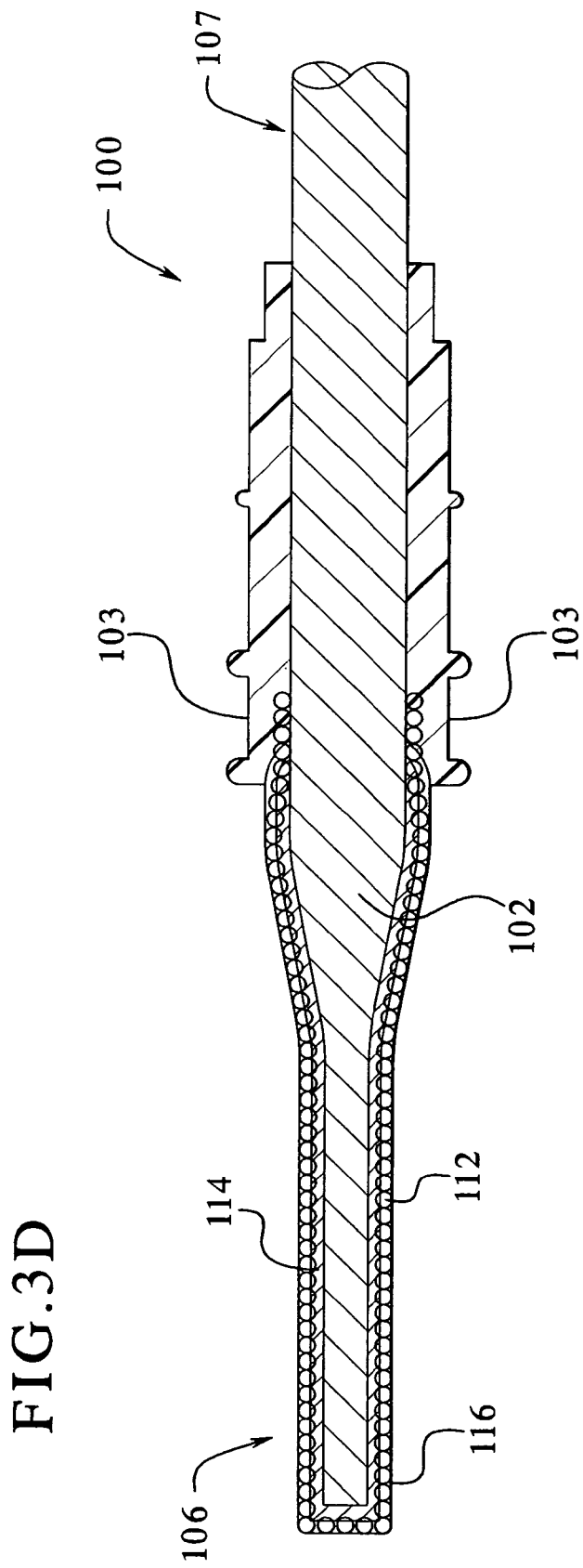
FIG. 3D is a cross-section view of the embodiment of FIG. 3C taken generally along the line 3D-3D.

In one embodiment, a top coating 116 is applied over the layer of epoxy modified rigid silicone powder particles 112 so that the top coating completely and fully coats the layer of epoxy modified rigid silicone powder particles on the surface of the electrode. This top coating may be applied to a semi-cured epoxy modified rigid silicone powder prior to the final bake. As shown in FIG. 3C, the top coating 116 is applied so that the epoxy modified rigid silicone powder particles are exposed at the surfaces of the electrode. Therefore, the electrosurgical electrode retains the benefits of minimizing the buildup of tissue or eschar on the surface of the electrode. In this embodiment, the top coating is not applied to the surfaces of the electrode covered by the insulative or plastic material 103 as shown in FIG. 3D. This fully exposes the maximum amount of epoxy modified rigid silicone powder particles underneath at least a portion of the insulative material 103.

Figure 4A:
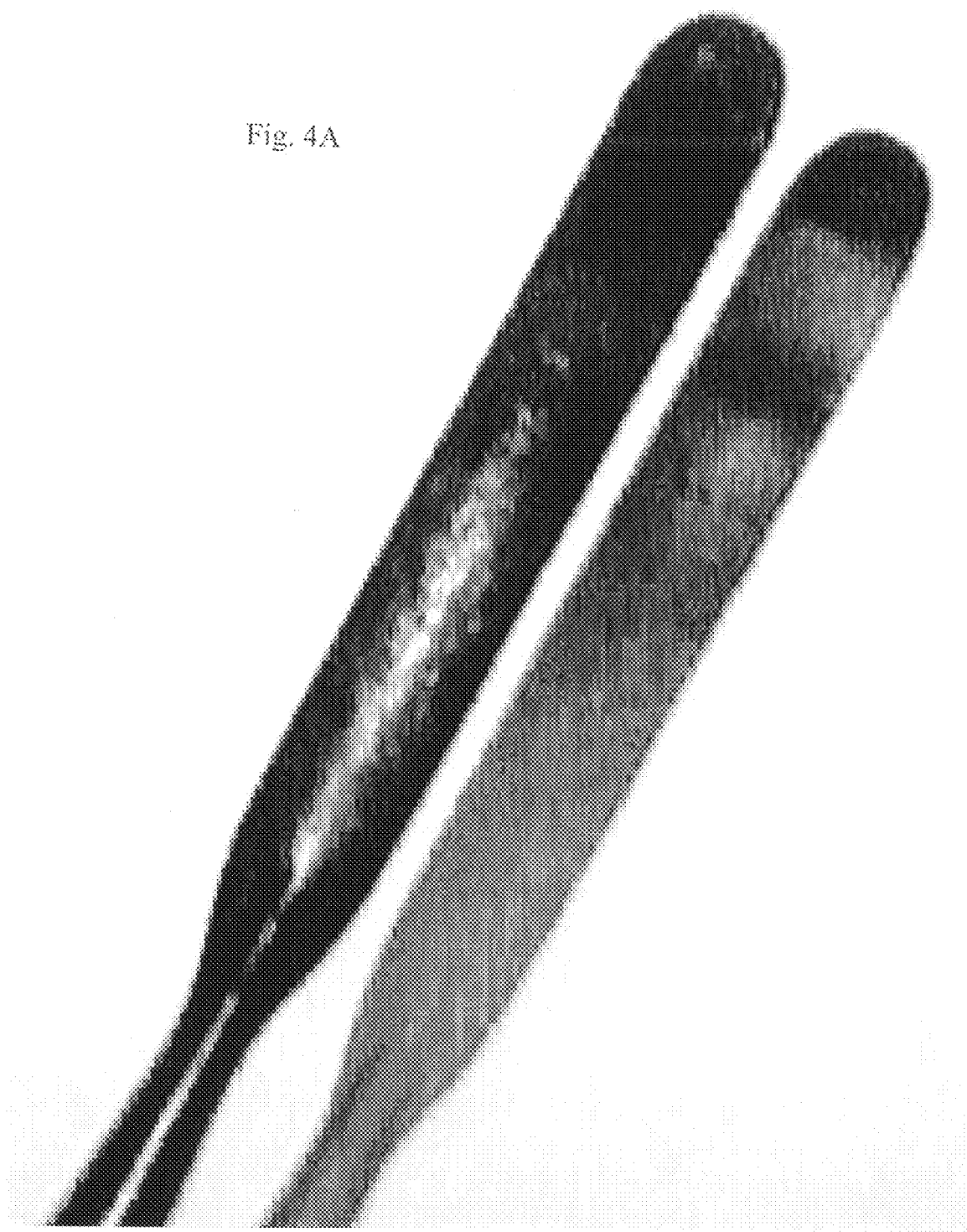
FIGS. 4A and 4B are color photographs illustrating stages of degradation of an electrosurgical device coated with polytetrafluoroethylene compared to an electrosurgical device coated with an epoxy modified rigid silicone powder.
Figure 4B:
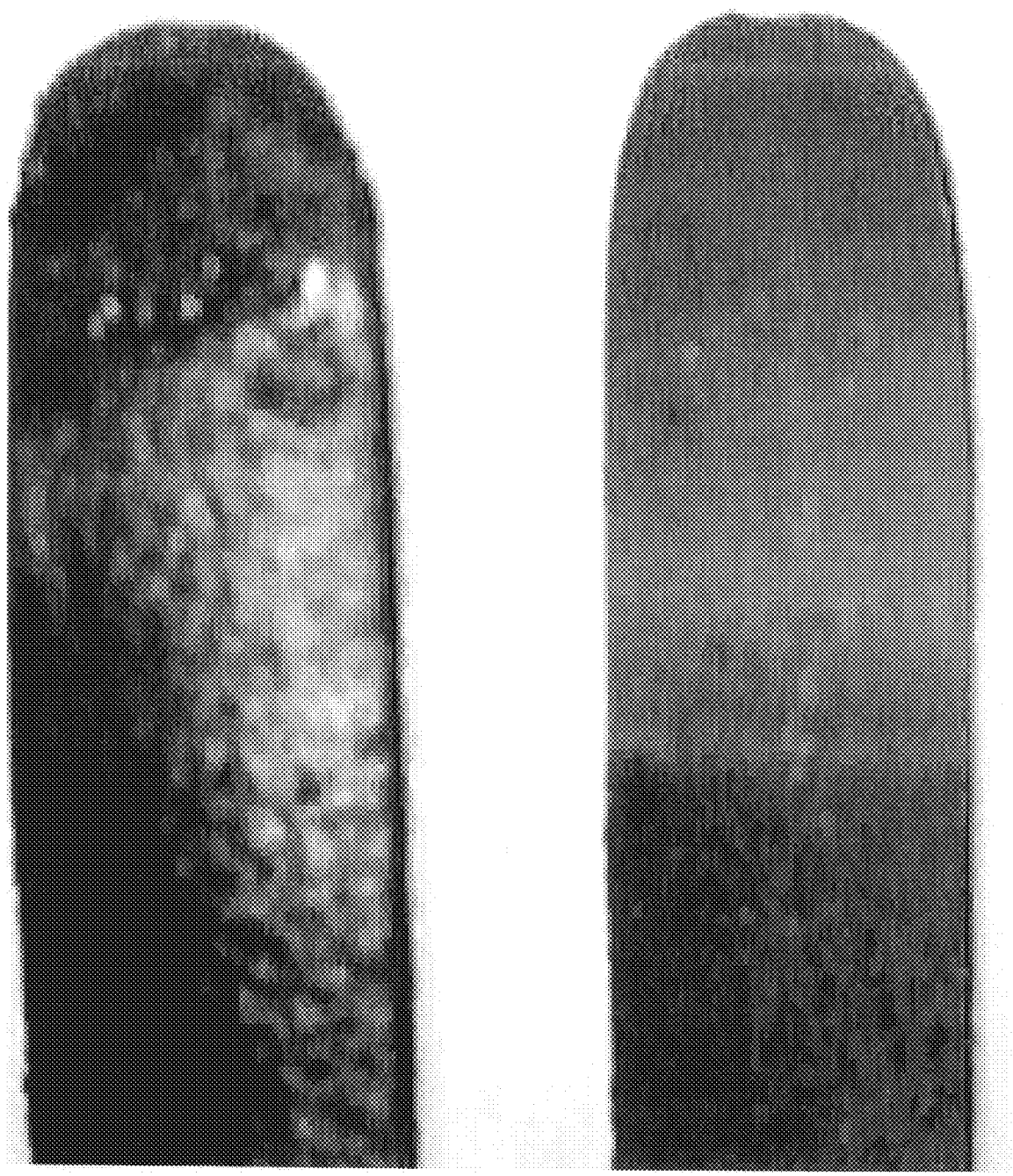

Referring now to FIGS. 4A and 4B, as described above, the high temperature resistance of the epoxy modified rigid silicone powder enables the electrosurgical electrode to be heated to temperatures above 500° F. (260° C.) which other non-stick coatings may break down, emit harmful byproducts and may micro-fracture during the decomposition. For example, FIGS. 4A to 4B illustrate the results of an experimental comparison between an electrosurgical device coated with polytetrafluoroethylene (PTFE), sold under the trade name DuPont Teflon® 851 204 (the left blade in FIGS. 4A and 4B) and an electrosurgical device coated with an epoxy modified rigid silicone powder (the black colored right blade in FIGS. 4A and 4B) after the two blades are each subjected to a "power" setting of between 5.0 and 9.0 kv and a "Coag" setting between 70 and 150 for a period of between 10 and 30 seconds using a ValleyLab generator, model Force 40S-20. It should be appreciated that the shown blades were not cleaned after a test cutting the same piece of calves liver (which is a common medical industry substitute for human flesh for electrosurgical testing). As seen in these figures, while the black colored epoxy modified rigid silicone powder coated blade substantially retains the epoxy modified rigid silicone powder coating (as seen as the shiny black color in the color photographs submitted to the U.S. Patent and Trademark Office), the PTFE coated blade exhibits substantial decomposition and discoloring of the green color PTFE, wherein the separate bands of discoloration of the green color on portion of the blade show the effect of elevated temperatures on the PTFE coated blade. Accordingly, unlike the PTFE coated blade, except at the tip or edge of the blade, there is substantially no deterioration or discoloration of the epoxy modified rigid silicone powder coating.

In one embodiment, in addition to the epoxy modified rigid silicone powder particles, a plurality of anti-microbial particles such as silver or silver compounds are applied to one or more of the surfaces of the electrosurgical device to reduce and kill bacteria and other potential germs that may be located on the surface(s) of the electrosurgical device. In one aspect of this embodiment, the anti-microbial particles are interspersed with the epoxy modified rigid silicone powder particles and a layer of anti-microbial material is applied to the electrosurgical device along with the epoxy modified rigid silicone powder particles. The above process can be repeated as necessary to maintain the effectiveness of the anti-microbial surface. The addition of the anti-microbial material tends to kill bacteria or other harmful organisms that contact the surface of the electrode during and after the surgical procedure. This coated electrode can be used multiple times in different surgical procedures without requiring sterilization (even though sterilization is preferred) because the anti-microbial particles kill the bacteria and other harmful organisms which contact the surfaces of the electrode. The coated electrosurgical device therefore minimizes the chance of infections or other complications in the body after the surgical procedure is complete.

In another embodiment, one or more additional epoxy modified rigid silicone powder layers are applied to the first or primary epoxy modified rigid silicone powder layer applied to the surface of the electrosurgical device to meet specific design specifications or coating requirements of a manufacturer. In this embodiment, the epoxy modified rigid silicone powder may be applied selectively to the electrosurgical device. For example, the epoxy modified rigid silicone powder may be applied to a long shank of a very long electrosurgical blade wherein the round shank is coated with two or more layers of the epoxy modified rigid silicone powder to create a thicker coating than a blade portion which is coated with one coat. In different embodiments, the additional bonding material layers may be the same or different than the first epoxy modified rigid silicone powder layer and are applied to the first epoxy modified rigid silicone powder layer until a predetermined thickness is achieved. Additionally, different materials may be added to the bonding material layer or layers, based on specific design specifications.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An electrosurgical electrode connectible to a handle, said electrosurgical electrode comprising:
a conductive substrate including a surface; and
a bonding material and at least one epoxy modified rigid silicone powder coating applied to at least a first portion of the surface of the substrate, said at least one epoxy modified rigid silicone powder coating including a plurality of epoxy modified rigid silicone powder particles each having a size of no greater than one-hundred-fifty microns.

2. The electrosurgical electrode of claim 1, wherein each of the epoxy modified rigid silicone powder particles includes a rigid silicone resin and a polysiloxane additive.

3. The electrosurgical electrode of claim 2, wherein the silicone resin is selected from the group consisting of: a phenyl polysiloxane powder resin, a methyl polysiloxane powder resin, a methyl phenyl siloxane powder resin, a phenyl silicone powder, a methyl phenyl silicone, a methyl phenyl polysiloxane powder resin and a phenyl alkyl polysiloxane powder resin.

4. The electrosurgical electrode of claim 2, wherein the polysiloxane additive is selected from the group consisting of: a methyl alkyl polysiloxane, a dimethyl polysiloxane and a methyl phenyl siloxane.

5. The electrosurgical electrode of claim 1, wherein each of the epoxy modified rigid silicone powder particles includes a rigid silicone resin.

6. The electrosurgical electrode of claim 5, wherein the silicone resin is selected from the group consisting of: a phenyl polysiloxane powder resin, a methyl polysiloxane powder resin, a methyl phenyl siloxane powder resin, a phenyl silicone powder, a methyl phenyl silicone, a methyl phenyl polysiloxane powder resin and a phenyl alkyl polysiloxane powder resin.

7. The electrosurgical electrode of claim 1, wherein each of the epoxy modified rigid silicone powder particles includes a polysiloxane additive.

8. The electrosurgical electrode of claim 7, wherein the polysiloxane additive is selected from the group consisting of: a methyl alkyl polysiloxane, a dimethyl polysiloxane and a methyl phenyl siloxane.

9. The electrosurgical electrode of claim 1, wherein the conductive substrate includes a metal.

10. The electrosurgical electrode of claim 9, wherein the metal includes stainless steel.

11. The electrosurgical electrode of claim 1, which includes an electrically insulative material applied to at least a second portion of the surface of the conductive substrate.

12. The electrosurgical electrode of claim 11, wherein the second portion of the surface of the conductive substrate underneath the electrically insulative material includes the epoxy modified rigid silicone powder coating.

13. The electrosurgical electrode of claim 1, wherein a plurality of anti-microbial particles are interspersed in said epoxy modified rigid silicone powder coating.

14. The electrosurgical electrode of claim 13, wherein the anti-microbial particles include at least one of the group consisting of: silver particles and ceramic particles.

15. The electrosurgical electrode of claim 1, which includes a single substantially uniform layer of the epoxy modified rigid silicone powder particles.

16. The electrosurgical electrode of claim 1, wherein the bonding material includes a primer.

17. The electrosurgical electrode of claim 1, wherein the bonding material includes an ultraviolet light cure resin.

18. The electrosurgical electrode of claim 1, wherein the bonding material includes an electron beam cure resin.

19. The electrosurgical electrode of claim 1, wherein the plurality of epoxy modified rigid silicone powder particles include a plurality of different sized epoxy modified rigid silicone powder particles.

20. The electrosurgical electrode of claim 1, which includes a top coat selected from the group consisting of: an abrasive resistant coating, a non-stick coating, an anti-microbial coating and an electrically conductive coating.

21. The electrosurgical electrode of claim 1, wherein at least part of the conductive substrate forms a shape selected from the group consisting of: a blade, a knife, a wire and a ball.

22. An electrosurgical electrode connectible to a handle, said electrosurgical electrode comprising:
a conductive substrate including a surface; and
a bonding material and at least one epoxy modified rigid silicone powder coating applied to at least a first portion of the surface of the substrate, wherein the epoxy modified rigid silicone powder coating includes: (i) a plurality of electrically conductive particles, and (ii) a plurality of epoxy modified rigid silicone powder particles each having a size of no greater than one-hundred-fifty microns.

23. An electrosurgical electrode connectible to a handle, said handle including at least one electrical transfer member configured to transfer electrical energy from an electrical source, said electrosurgical electrode comprising:
a conductive substrate configured to receive said electrical energy; and
a bonding material and at least one layer of epoxy modified rigid silicone powder applied to at least a first portion of a surface of the substrate, said epoxy modified rigid silicone powder including a plurality of epoxy modified rigid silicone powder particles each having a size of no greater than one-hundred-fifty microns.

24. The electrosurgical electrode of claim 23, wherein each of the epoxy modified rigid silicone powder particles includes a rigid silicone resin and a polysiloxane additive.

25. The electrosurgical electrode of claim 24, wherein the silicone resin is selected from the group consisting of: a phenyl polysiloxane powder resin, a methyl polysiloxane powder resin, a methyl phenyl siloxane powder resin, a phenyl silicone powder, a methyl phenyl silicone, a methyl phenyl polysiloxane powder resin and a phenyl alkyl polysiloxane powder resin.

26. The electrosurgical electrode of claim 24, wherein the polysiloxane additive is selected from the group consisting of: a methyl alkyl polysiloxane, a dimethyl polysiloxane and a methyl phenyl siloxane.

27. The electrosurgical electrode of claim 23, wherein each of the epoxy modified rigid silicone powder particles includes a rigid silicone resin.

28. The electrosurgical electrode of claim 27, wherein the silicone resin is selected from the group consisting of: a phenyl polysiloxane powder resin, a methyl polysiloxane powder resin, a methyl phenyl siloxane powder resin, a phenyl silicone powder, a methyl phenyl silicone, a methyl phenyl polysiloxane powder resin and a phenyl alkyl polysiloxane powder resin.

29. The electrosurgical electrode of claim 23, wherein each of the epoxy modified rigid silicone powder particles includes a polysiloxane additive.

30. The electrosurgical electrode of claim 29, wherein the polysiloxane additive is selected from the group consisting of: a methyl alkyl polysiloxane, a dimethyl polysiloxane and a methyl phenyl siloxane.

31. The electrosurgical electrode of claim 23, wherein the conductive substrate includes a metal.

32. The electrosurgical electrode of claim 31, wherein the metal includes stainless steel.

33. The electrosurgical electrode of claim 23, wherein the epoxy modified rigid silicone powder includes a plurality of anti-microbial particles.

34. The electrosurgical electrode of claim 33, wherein the anti-microbial particles include at least one of the group consisting of: silver particles and ceramic particles.

35. The electrosurgical electrode of claim 33, which includes an electrically insulative material applied to at least a second portion of the surface of the conductive substrate.

36. The electrosurgical electrode of claim 33, wherein the second portion of the surface of the conductive substrate underneath the electrically insulative material is coated with the epoxy modified rigid silicone powder.

37. The electrosurgical electrode of claim 23, wherein the bonding material includes a primer.

38. The electrosurgical electrode of claim 23, which includes a single substantially uniform layer of the epoxy modified rigid silicone powder particles.

39. The electrosurgical electrode of claim 23, wherein the bonding material includes an ultraviolet light cure resin.

40. The electrosurgical electrode of claim 23, wherein the bonding material includes an electron beam cure resin.

41. The electrosurgical electrode of claim 23, wherein the epoxy modified rigid silicone powder includes at least one electrically conductive pigment.

42. The electrosurgical electrode of claim 23, wherein the plurality of epoxy modified rigid silicone powder particles include a plurality of different sized epoxy modified rigid silicone powder particles.

43. The electrosurgical electrode of claim 23, which includes a top coat selected from the group consisting of: an abrasive resistant coating, a non-stick coating, an anti-microbial coating and an electrically conductive coating.

44. The electrosurgical electrode of claim 23, wherein at least part of the conductive substrate forms a shape selected from the group consisting of: a blade, a knife, a wire and a ball.

45. The electrosurgical electrode of claim 23, wherein said conductive substrate includes a proximal end connectible to the handle.

46. A method of coating an electrosurgical device including a conductive substrate, said method comprising the steps of:
   (a) applying a wet bonding material to at least a first portion of a surface of the conductive substrate;
   (b) applying an epoxy modified rigid silicone powder coating to the wet bonding material, said epoxy modified rigid silicone powder coating including a plurality of epoxy modified rigid silicone powder particles each having a size of no greater than one-hundred-fifty microns; and
   (c) at least partially curing the wet bonding material and the epoxy modified rigid silicone powder coating.

47. The method of claim 46, wherein the wet bonding material includes a primer.

48. The method of claim 46, which includes the step of repeating (a) to (c) until a desired thickness is achieved.

49. The method of claim 46, wherein the epoxy modified rigid silicone powder coating includes a plurality of anti-microbial particles.

50. The method of claim 49, wherein the anti-microbial particles include at least one of the group consisting of: silver particles and ceramic particles.

51. The method of claim 46, which includes applying an electrically insulative material to at least a second portion of the surface of the conductive substrate.

52. The method of claim 51, which includes applying the epoxy modified rigid silicone powder coating to the second portion of the surface of the conductive substrate underneath the insulative material.

53. The method of claim 46, wherein each of the epoxy modified rigid silicone powder particles includes a rigid silicone resin and a polysiloxane additive.

54. The method of claim 53, wherein the silicone resin is selected from the group consisting of: a phenyl polysiloxane powder resin, a methyl polysiloxane powder resin, a methyl phenyl siloxane powder resin, a phenyl silicone powder, a methyl phenyl silicone, a methyl phenyl polysiloxane powder resin and a phenyl alkyl polysiloxane powder resin.

55. The method of claim 53, wherein the polysiloxane additive is selected from the group consisting of: a methyl alkyl polysiloxane, a dimethyl polysiloxane and a methyl phenyl siloxane.

56. The method of claim 46, wherein each of the epoxy modified rigid silicone powder particles includes a rigid silicone resin.

57. The method of claim 56, wherein the silicone resin is selected from the group consisting of: a phenyl polysiloxane powder resin, a methyl polysiloxane powder resin, a methyl phenyl siloxane powder resin, a phenyl silicone powder, a methyl phenyl silicone, a methyl phenyl polysiloxane powder resin and a phenyl alkyl polysiloxane powder resin.

58. The method of claim 46, wherein each of the epoxy modified rigid silicone powder particles includes a polysiloxane additive.

59. The method of claim 58, wherein the polysiloxane additive is selected from the group consisting of: a methyl alkyl polysiloxane, a dimethyl polysiloxane and a methyl phenyl siloxane.

60. The method of claim 46, wherein the wet bonding material includes an ultraviolet light cure resin.

61. The method of claim 46, wherein the wet bonding material includes an electron beam cure resin.

62. The method of claim 46, wherein the plurality of epoxy modified rigid silicone powder particles include a plurality of different sized epoxy modified rigid silicone powder particles.

63. The method of claim 46, which includes applying a top coat to the epoxy modified rigid silicone powder coating, said top coat selected from the group consisting of: an abrasive resistant coating, a non-stick coating, an anti-microbial coating and an electrically conductive coating.

64. The method of claim 46, which includes evenly applying the epoxy modified rigid silicone powder particles to the wet bonding material.

65. A method of coating an electrosurgical device including a conductive substrate, said method comprising the steps of:
   (a) applying a wet bonding material to at least a first portion of a surface of the conductive substrate;
   (b) applying an epoxy modified rigid silicone powder coating to the wet bonding material; wherein the epoxy modified rigid silicone powder coating includes: (i) at least one electrically conductive particle, and (ii) a plurality of epoxy modified rigid silicone powder particles each having a size of no greater than one-hundred-fifty microns; and
   (c) at least partially curing the wet bonding material and the epoxy modified rigid silicone powder coating.

66. A method of coating an electrosurgical device including a conductive substrate, said method comprising the steps of:
   (a) applying a wet bonding material to at least a first portion of a surface of the conductive substrate,
   (b) charging a plurality of epoxy modified rigid silicone powder particles before applying a coating of the plurality of epoxy modified rigid silicone powder particles to the wet bonding material,
   (c) grounding the conductive substrate and the applied wet bonding material before applying the coating of the plurality of epoxy modified rigid silicone powder particles to the wet bonding material, (d) electrostatically applying the coating of the epoxy modified rigid silicone powder particles to the wet bonding material, and
(e) at least partially curing the wet bonding material and the epoxy modified rigid silicone powder coating.

* * * * *